(12) United States Patent
Ugolin et al.

(10) Patent No.: US 8,211,693 B2
(45) Date of Patent: Jul. 3, 2012

(54) DEVICE FOR SEPARATING AND/OR ANALYZING SEVERAL MOLECULAR TARGETS DISSOLVED IN A COMPLEX MIXTURE

(75) Inventors: Nicolas Ugolin, Paris (FR); Sylvie Chevillard, Le Kremlin-Bicetre (FR); Catherine Ory, Paris (FR); Jerome Lebeau, Paris (FR)

(73) Assignee: Commissariat a l'Energie Atomique, Paris (FR)

( * ) Notice: Subject to any disclaimer, the term of this patent is extended or adjusted under 35 U.S.C. 154(b) by 0 days.

(21) Appl. No.: 12/700,680

(22) Filed: Feb. 4, 2010

(65) Prior Publication Data

US 2010/0203540 A1    Aug. 12, 2010

Related U.S. Application Data

(60) Division of application No. 11/386,781, filed on Mar. 23, 2006, now Pat. No. 7,687,257, which is a continuation of application No. PCT/FR2004/002207, filed on Aug. 27, 2004.

(51) Int. Cl.
*C12M 1/34* (2006.01)
(52) U.S. Cl. .................................................. 435/287.1
(58) Field of Classification Search .................. None
See application file for complete search history.

(56) References Cited

U.S. PATENT DOCUMENTS

| | | | |
|---|---|---|---|
| 5,595,498 A * | 1/1997 | Jego et al. ................... 439/342 |
| 5,871,918 A | 2/1999 | Thorp et al. |
| 5,872,010 A * | 2/1999 | Karger et al. ................ 436/173 |
| 6,106,685 A * | 8/2000 | McBride et al. ............. 204/600 |
| 6,131,410 A | 10/2000 | Swierkowski et al. |
| 6,143,152 A | 11/2000 | Simpson et al. |
| 6,294,063 B1 | 9/2001 | Becker et al. |
| 6,391,590 B1 * | 5/2002 | Sano et al. ................... 435/69.7 |
| 6,458,259 B1 * | 10/2002 | Parce et al. .................. 204/454 |
| 6,548,311 B1 | 4/2003 | Knoll |
| 6,613,525 B2 | 9/2003 | Nelson et al. |
| 6,635,452 B1 * | 10/2003 | Monforte et al. ............ 506/9 |
| 6,649,419 B1 * | 11/2003 | Anderson ..................... 436/526 |
| 6,676,819 B1 * | 1/2004 | Liu et al. ...................... 204/451 |
| 2002/0090649 A1 | 7/2002 | Chan et al. |
| 2002/0106644 A1 * | 8/2002 | Rosenow ...................... 435/6 |
| 2002/0127740 A1 | 9/2002 | Ho |
| 2003/0044832 A1 | 3/2003 | Blankenstein |
| 2003/0044864 A1 * | 3/2003 | Short et al. ................... 435/7.23 |
| 2004/0018611 A1 * | 1/2004 | Ward et al. ................... 435/287.2 |
| 2004/0189311 A1 | 9/2004 | Glezer et al. |

FOREIGN PATENT DOCUMENTS

| | | |
|---|---|---|
| WO | WO-82/02211 A1 | 7/1982 |
| WO | WO 02/34951 A2 | 5/2002 |
| WO | WO 03/016574 A1 | 2/2003 |
| WO | WO 03/033722 A2 | 4/2003 |
| WO | WO-2004/059301 A1 | 7/2004 |

OTHER PUBLICATIONS

European Search Report issued in corresponding European Application No. 10 15 5815 on Jul. 22, 2010.
Sauer S et al: "Genotyping single-nucleotide polymorphisms by matrix-assisted laser-desorption/ionization time-of-flight mass spectrometry" Journal of Chromatography B: vol. 782, No. 1-2, Dec. 25, 2002 pp. 73-87.

* cited by examiner

*Primary Examiner* — Ann Lam
(74) *Attorney, Agent, or Firm* — Birch, Stewart, Kolasch & Birch, LLP.

(57) ABSTRACT

The invention relates to a device for separating and/analyzing several molecular targets dissolved in a complex mixture which is characterized in that it comprises
  a) a matrix of micro-columns, wherein each micro-column (2) comprises an immobilized molecular probe for retaining a specific molecular target contained in the complex mixture by specific probe/target linkage,
  b) a first capillary network (3) for circulating the complex mixture introduced into the inventive device towards each micro-column of the matrix defined in a),
  c) a second capillary network (4) for circulating, after elution, the molecular targets retained on the micro-columns towards a sensor (5) for carrying out the recovery and/or analysis thereof, and
  d) if necessary, a sensor (5), preferably in the form of a mass spectrometer, for carrying out the recovery and/or analysis of different molecular targets.

12 Claims, 16 Drawing Sheets

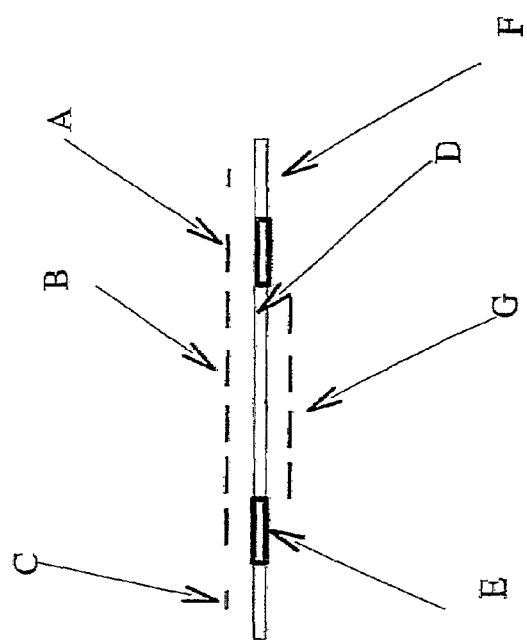
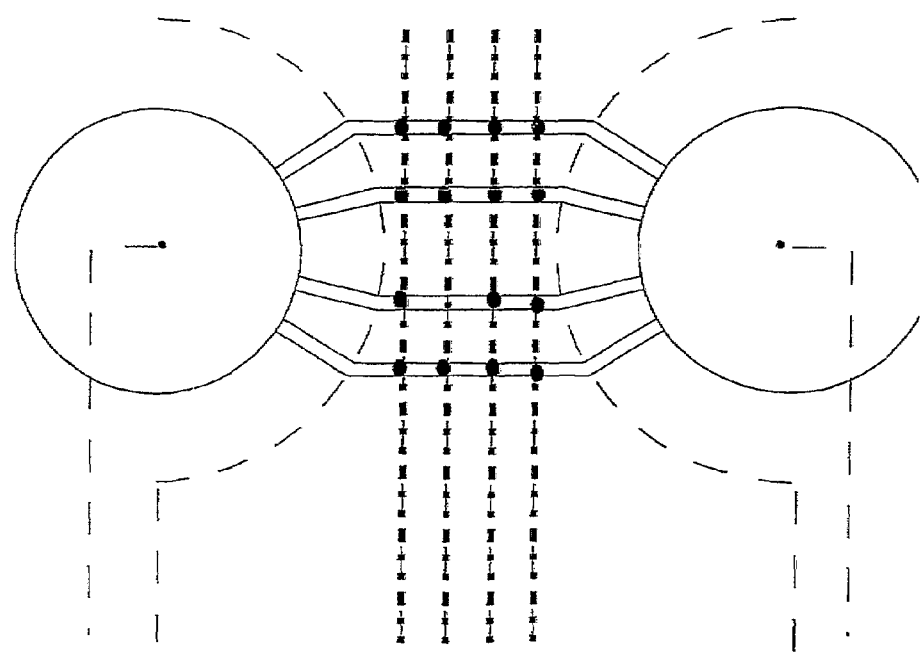
fig. 11

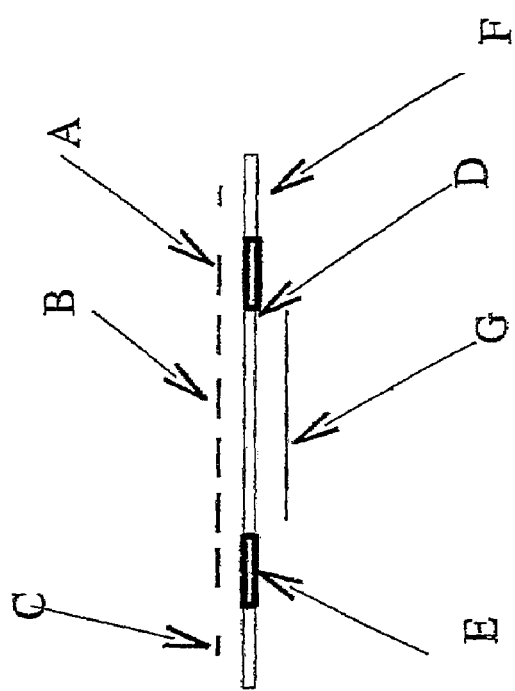
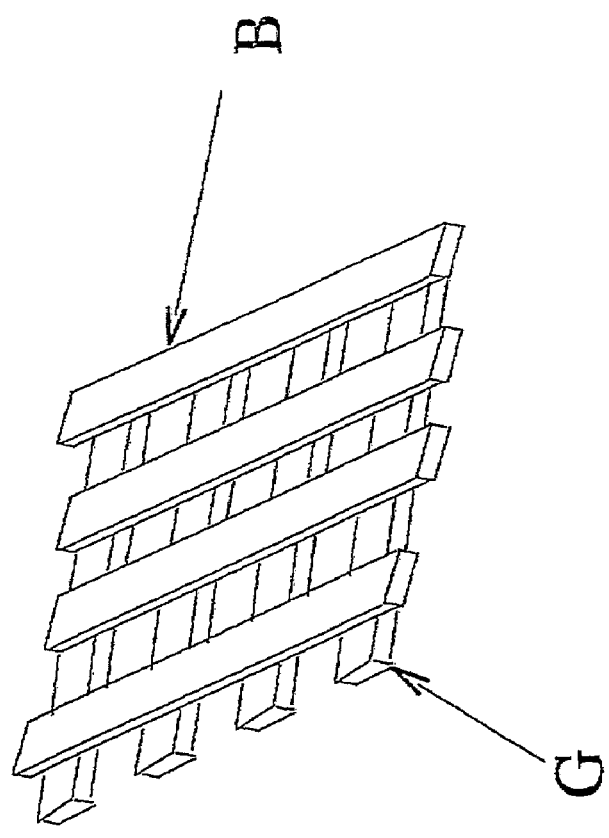
fig. 17

DEVICE FOR SEPARATING AND/OR ANALYZING SEVERAL MOLECULAR TARGETS DISSOLVED IN A COMPLEX MIXTURE

This application is a Divisional of application No. 11/386,781 filed on Mar. 23, 2006 now U.S. Pat. No. 7,687,257, and for which priority is claimed under 35 U.S.C. § 120. Application No. 11/386,781 is the continuation of PCT International Application No. PCT/PCT/FR2004/002207 filed on Aug. 27, 2004 under 35 U.S.C. § 371. The entire contents of each of the above-identified applications are hereby incorporated by reference. This application also claims priority of Application No. 0311204 filed in France on Sep. 24, 2003, under 35 U.S.C. § 119.

The invention relates to a device for separating and/or analyzing a plurality of molecular targets in solution in a complex mixture, in particular nucleic acids or proteins. The invention relates in particular to a device comprising an organized array or matrix of biopolymer probes for the separation or analysis of molecular targets. Such a device separates and/or detects a plurality of molecular targets in solution in a complex mixture. In a first embodiment of the invention, a device comprises:

a. a matrix of micro-columns comprising N rows and P columns of micro-columns disposed in the same plane, each micro-column comprising an immobilized molecular type probe which can retain a specific molecular target present in the complex mixture. In accordance with one embodiment of the invention, this is by specific probe/target binding;

b. a first network of capillaries located in a plane parallel to the plane of the micro-column matrix, above the micro-column matrix, said first network allowing movement of a complex mixture introduced into the device towards each micro-column of the matrix defined in a);

c. a second network of capillaries located in a plane parallel to the plane of the micro-column matrix, below the micro-column matrix, said second network allowing movement of molecular targets, after elution, towards one or more detector(s), allowing their recovery and/or analysis;

d. if necessary, a detector allowing recovery and/or analysis of the various molecular targets, preferably a mass spectrometer.

The invention also pertains to a device for separating and/or detecting a plurality of molecular targets in solution in a complex mixture, said device comprising:

a. a network of capillaries allowing movement of a complex mixture introduced into the device;

b. two sets of electrodes disposed either side of the network of capillaries;
   a set of functionalized electrodes, the electrodes of which are grafted to probes organized into spots, each probe being capable of retaining a specific molecular target present in the complex mixture, by specific probe/target binding;
   a set of non-functionalized electrodes.

The invention also concerns the uses of said device, in particular for separating and/or analyzing DNA or RNA molecules contained in a biological sample.

Determining the mass of macromolecules such as DNA, RNA or proteins using mass spectrometric analysis is known. If analysis using that method is accompanied by controlled decomposition of the molecules, their sequence may also be determined. However, for mixtures of molecules with differing sizes and sequences, it becomes difficult or even impossible to discriminate between the various molecules using that technique.

Other methods may be used as an alternative to mass spectrometry.

Surface plasmon resonance (SPR) can determine the density of the material accumulated a short distance (less than 200 nm) from the surface of a thin sheet (x nm) of metal with free electrons such as gold or platinum. Reflection from one of the faces of the metal sheet is modified in proportion to the density and quantity of the material close to the other face. However, it is not actually possible to distinguish between the various types of molecules contributing to modification of the reflection. Further, at the moment, the detection sensitivity and binding of the targets to the bioarrays using that method is lower than the detection sensitivity achieved in fluorescence with labeled molecules. Even the presence of probes on the metal surface reduces the detection sensitivity by spacing the targets from the metal. During dynamic measurements of the target/probe interaction, the presence of free target molecules close to the surface falsifies the measurement. To be effective, detection by SPR methods generally necessitates more instrumentation than that required for fluorescent or radioactive labeling methods. For that reason, SPR detection remains incompatible with some experiments, in particular in the field of diagnostics.

Further, the variation in the impedance existing between different molecular states may be measured.

A single strand DNA molecule with a given sequence does not have the same impedance as the corresponding paired double strand complex. That property is used for DNA arrays to evaluate the degree of hybridization and thus the number of probe-target complexes formed on the bio-array (ref). In general, impedance variations may be used to study intermolecular interactions such as binding of a ligand to its receptor, but also interactions between DNA molecules or proteins and a drug, ion, etc. However, for bioarrays, this detection method is limited:

1) by the difficulty in producing high density arrays with more than 2000 spots. Because of the size of the electrodes and the geometry of the connections used to produce impedance arrays, the hybridization surface becomes very large as soon as the number of spots exceeds 800. However, a large hybridization surface implies a large sample volume which has to cover the hybridization surface, hence the need for a large quantity of biological material to reach the minimum concentration for detection. This is incompatible with experiments in which only a small amount of material is available, such as in diagnostics;

2) by changes in the conformation of the study molecules (probe and/or target), which causes measurement artifacts rendering the measured impedance values impossible to interpret. As an example, deformations in DNA due to the sequence or intramolecular hybridizations causes variations in impedance of the same order of magnitude as for hybridization.

Field effect transistors are used in the prior art as current amplifiers to measure the variation in impedance linked to hybridization of the DNA molecule (ref). The probes are grafted to the transistor gate. When the targets bind, they modify the impedance of the gate and cause a modification to the current between the source (transistor inlet) and the drain (transistor outlet). However, no networked organization has yet been described for that type of detector. The fact of using a field effect transistor as a current amplifier limits the frequency of the alternating currents which can be used to highlight variations in impedance linked to hybridization, further limiting the sensitivity of the detector (ref). Further, in such prior art descriptions, the gate controls the passage of current into the transistor, and the fact of grafting the probes thereto does away with the possibility of using the various terminals of the transistor as electrodes to control the movement of targets and thus to direct hybridization by concentrating the targets at the probes.

Organized matrices of biopolymer probes (DNA arrays, protein arrays, etc) can qualitatively and quantitatively separate biopolymers present in a mixture, theoretically regardless of their number, sequences and complexity. However, nucleic acid networks, for example, cannot absolutely and accurately count the number of hybridized molecules. Further, using currently available technology, detection of biopolymers on micro-arrays is indirect, necessitating a step for labeling them (fluorescence, radioactivity, etc). While the yields for incorporation of radiolabeled and cold residues into biopolymers are almost the same, this is not the case with fluorescent labels (Martinez et al, Nucl Acids Res, 2003, 31: p. 18; Hoen et al—Nucleic Acid Res, 2003, Mar. 1; 31(5); p 20). Such problems with labeling are encountered when synthesizing cDNA molecules incorporating the fluorescent markers CY3 and CY5. The steric hindrance resulting from this last type of labeling can also considerably modify the kinetics and stoichiometric equilibria for the reactions (hybridization, antibody-antigen reaction, target-ligand reaction in general). Such steric hindrance problems are eliminated when radioactive isotopes are used; however, radioactive isotopes require radioactive waste management. Further, techniques for detecting radioactively labeled molecules, i.e. essentially of the phosphoimager type for radioactivity (Bertucci F et al—Hum Mol Genet 1999 September; 8(9): 1715-22. Erratum in: Hum Mol Genet 1999 October; 8(11); p 2129), and the various types of scanner for the detection of fluorescence have a certain number of limitations as regards the quantity of biological material to be hybridized on an array to reach the detection thresholds and reproducibility requirements for the measurements made. In fact, it is not possible to detect molecules present in an amount of a few copies per cell from samples having a small number of cells (~1000 cells), which nevertheless corresponds to a frequent situation for clinical samples.

An alternative to using a conventional DNA array consists of functionalizing the interior of a capillary with probes disposed in rings all along it, each ring being constituted by a probe type specific to a gene. The small diameter of the capillary (~100 μm) in theory allows the volume of the sample to be analyzed to be reduced and thus the concentration which can be detected by fluorescence can be reached, for example with a smaller quantity of labeled biological material. However, even when the reaction volume is reduced, the concentration of each target which hybridizes at a ring of probes is dependent on the whole of the capillary volume. The larger the number of probes, the longer must be the capillary length and the larger must be the quantity of material (for example of sample to be analyzed) required to achieve a detectable concentration (the volume of the capillary being proportional to its length). The problems linked to labeling samples are the same when using capillaries. Further, fabricating a functionalized capillary with a large number of different probes is complicated and expensive.

Finally, DNA or protein arrays described in the prior art are generally for single use, which generates very high operational costs for each experimental point. This disposability significantly limits generalization of such techniques to studies and clinical tests for diagnostic ends.

The present invention provides a device for separating and/or analyzing specific molecular targets present in a complex mixture, in particular biopolymers such as RNA, DNA or protein molecules. The device of the invention can be re-used for a large number of experiments and allows product concentrations of the order of an attomole ($10^{-18}$) or even a zeptomole ($10^{-21}$) to be measured. These limitations allow molecules present as a single copy per cell to be identified from a limited number of cells, for example a thousand to even a hundred cells. Further, in certain implementations of the invention, the device can carry out comparative analyses, and thus can analyze several samples simultaneously. In a further implementation, the device can directly determine the nucleic acid sequence or the proteins retained by the probes, for example in each micro-column of the matrix or hybridization spot on the matrix.

Thus, in a first aspect, the invention pertains to a device for separating and/or analyzing a plurality of molecular targets in solution in a complex mixture, said device comprising:
  a. a matrix of micro-columns comprising N rows and P columns of micro-columns disposed in the same plane, each micro-column comprising an immobilized molecular type probe which can retain a specific molecular target present in a complex mixture by specific probe/target binding;
  b. a first network of capillaries located in a plane parallel to the plane of the micro-column matrix, above the micro-column matrix, said first network allowing movement of a complex mixture introduced into the device towards each micro-column of the matrix defined in a);
  c. a second network of capillaries located in a plane parallel to the plane of the micro-column matrix, below the micro-column matrix, said second network allowing movement of molecular targets, after elution, towards one or more detector(s), allowing their recovery and/or analysis;
  d. if necessary, a detector allowing recovery and/or analysis of the various molecular targets, preferably a mass spectrometer.

If appropriate, electrode systems can control/displace the targets in the networks.

The term "capillary" means any appropriate channel for allowing the movement of fluids, with a diameter of less than 1 millilitre, preferably in the range 1 to 100 μm.

Within the context of the invention, the term "separation of molecular targets in a complex mixture" means the operation which can obtain, in distinct volumes, solutions enriched in specific molecules or molecular targets initially present in a complex mixture. The term "enriched" means that the molecular targets represent at least 50% of the molecules present in the solution, obtained after separation, preferably 80%, more preferably at least 90%.

The term "molecular target analysis" means the operation which consists of identifying the presence of the molecular target (detection) and/or the relative or absolute quantity of said molecular target in a complex mixture to be analyzed (assay).

The expression "complex mixture" as used in the invention means a solution containing a large number of molecules with different structures, in particular a mixture of more than 100 molecules having different structures. The device of the invention is more preferably intended for separation and/or analysis of biological molecules (or biomolecules) contained in a sample of biological origin.

More particularly, it may be a sample from tissue or a biological fluid such as blood, plasma, or cephalorachidian liquid, urine or saliva. The sample may be taken from an animal (in particular a mammal, preferably human). The sample may in particular be taken from a healthy individual or from a patient with a disease. The disease may in particular be a cancer, a neuro-degenerative disease, or an infectious disease, in particular a viral, bacterial or parasitic disease. The sample may also contain a tissue extract or a cellular extract, derived from eukaryotic or prokaryotic cells, from bacteria, fungi or yeasts, in particular cells in culture or cells sampled from the external environment. The sample may also be obtained from a plant. It may also be a sample from an agro-alimentary product, in particular cooked food, or from grain, fruit or cereal.

The device may thus be used in a variety of applications, in particular for medical diagnostics or agro-alimentary quality control, or for any biological analysis, in the fields of ecology, archeology or criminology.

Each micro-column of the device of the invention comprises a cell of any form, for example tubular in shape, preferably having a diameter of 2 to 1000 µm, preferably 20 to 100 µm, with a length of 2 to 2000 µm, preferably 40 to 200 µm.

Each cell is connected via first end to a capillary of a first capillary network and to a capillary of the second capillary network via its opposite end, so that it is possible to traverse the set of cells with a flow moving in the network of capillaries.

The device is generally constituted by a matrix of N rows and P columns of cells disposed in the same plane. The cells may be inclined at any angle to this plane, but are preferably parallel or perpendicular to the plane of the matrix for practical reasons. For spacing reasons, the cells may be disposed so that adjacent rows are staggered.

The cells may in particular be hollowed out or molded into the thickness of a surface of a suitable material for producing the device of the invention, such as glass, silicon, plastic, Kapton, carbon, gold or any other material forming the plane of the matrix.

The matrix of micro-columns of the device of the invention is thus constituted by a large number of cells, for example 1 to a million cells, preferably 100 to 100000 cells, thus allowing separation and/or analysis of as many specific molecular targets as may be contained in a single sample.

The molecular probes are disposed and immobilized in each cell, preferably with one probe of particular specificity in each cell, thereby forming chromatographic micro-columns which can each retain a specific molecular target.

The term "immobilized" as used in the invention means that the probes are maintained in the cells, in particular in the presence of an electric or magnetic field or a moving stream which has been injected into the capillary network entering the device when it traverses the micro-columns containing the molecular probes.

The device is thus composed of a matrix of micro-columns in which each micro-column comprises a large quantity (for example $10^6$ to $10^{10}$) of probes of the same specificity, immobilized and capable of specifically binding the corresponding molecular targets under appropriate conditions. Said probes will hereinafter be termed "molecular probes". The term "specific binding" used with reference to binding of a probe with a target contained in the complex mixture means that the probe binds with a particular target but does not bind in a significant manner with the other molecules, and more particularly the other targets present in the complex mixture.

Preferred probe-target pairs are nucleic acids hybridizing with complementary sequences such as messenger RNA, RNA or cDNA molecules hybridizing with specific oligonucleotide probes, antigens specifically recognizing probes constituted by antibodies or their functional fragments, or any receptor-ligand or ligand-receptor pair.

The skilled person could adapt said device for separating and/or analyzing any type of molecule as long as it is possible to associate with them an entity which specifically recognizes them, constituting a molecular probe, the target molecules being capable of specifically binding to said molecular probe which can be immobilized on a support.

The probes can be immobilized in each cell by means of a strong interaction with an element which cannot leave the cell, for example. The coupling mode consists, for example, of immobilizing probes on the inner wall of the cell, in particular by covalent bonding or any other strong interaction.

As an alternative, the molecular probes may be fixed to particles the structure of which is such that they cannot escape from their cell (Huang et al, Anal Chem; 2002, 74(14): p 3362-3371; Ugolin et al—FR-A-0015398, November 2000). The mean particle diameter will, for example, be greater than the diameter of the capillaries at the inlet and outlet to/from each micro-column. The particles may be retained in the cell by magnetic interaction between the particles and part of the inner wall of the cell, if the particles are capable of tolerating or supplying magnetic attraction and if a part of the wall of the cell is, in contrast, capable of providing or being subjected to magnetic attraction.

In a particular embodiment, the molecular probes are immobilized in a gel contained in each cell, preventing migration of said molecular probes from the micro-column. The molecular probes are, for example, retained by strong interaction or covalent bonding with the molecules forming the gel.

In a preferred embodiment, each cell is filled with a gel and the molecular probes are coupled to particles the diameter of which is greater than the mesh of the gel, immobilizing particles in the micro-columns and thus immobilizing the molecular probes coupled therewith.

Any appropriate method for coupling molecular probes to particles or to the inner wall of the cell may be used. Examples which can in particular be cited are non covalent biotin-avidin type coupling between molecular probes coupled to biotin and beads functionalized with avidin, such as those sold by "Dynal" (Dynal worldwide distributors, copyright 1996, Dynal AS-Technical Handbook second edition).

In general, any type of coupling, chemical bond, or strong interaction described for chromatographic columns may be suitable.

The probes may in particular be fixed directly to the polymers of a gel contained in each micro-column.

In a further embodiment, in particular in the case in which the probe is a nucleic acid, for covalent coupling of said probes to a particle, it is possible to synthesize a polyX/probe heteropolymer such as polypyrrole/nucleic acid. In fact, nucleic acid molecular probes bound to pyrrole at the 5' or 3' end have the ability of polymerizing with free molecules of pyrrole, thereby forming a heteropolymer, heteropolymers of sufficient size being able to act as the particles described above.

Another alternative is to use nucleic acid probes bonded at the 5' and/or 3' end to bridging agents such as psoralenes. The sequences of the probes may be in the form: psoralene 5'(Y1) Xn(Y2)3'. Xn represents the probe proper and Y1 and Y2 are sequences selected so that the probes can concatenate without limit to each other by complementarity. As an example, the probes to be polymerized may be constituted by an equimolar mixture of psoralene 5'(T)mXn(A)m3' in which m=5. Under ultraviolet radiation, the probes polymerize into a macro molecule (poly5'(T)mXn(T)m3 psoralene3'(A)m(X)n (A)m5' ... ), which can be retained in each cell.

When fixing the probes directly to the cell wall, all of the interaction types described above may also be suitable. In particular, interactions routinely used in DNA arrays to bind nucleic acid probes or protein arrays to bind polypeptide probes may also be adapted (lysine/nucleic acid electrostatic interaction, silane binding, polymerization of pyrrole on the cell surface, psoralene binding, etc), in similar manner to the in situ synthesis methods on beads or cell walls. The use of nylon or nitrocellulose could also be envisaged to bind the probes irreversibly to the particles or the walls of the cells (particles or walls which are then produced from those materials). Binding may be direct or may be carried out by bridging, such as a psoralene bridge between a nylon particle and the molecular probe.

In a particular embodiment, the molecular probes coupled to particles in the cell may also be mechanically retained by using filters perforated with pores of a sufficiently small diameter (for example, a diameter less than the diameter of the filtered particles). Such filters are in routine use and are commercially available (Teflon filter, etc).

Immobilizing the molecular probes on their support must be sufficiently strong to resist the various treatments applied and any electrical fields used to manipulate the targets.

When the device of the invention comprises one or more capillary networks connected to electrodes which can control elution and/or migration of the targets to be analyzed, the probes may be fixed to electrodes using any of the chemical processes described for fixing probes to a bioarray support. In the case of electrodes of ITO (or any other transparent alloy, ATO, ZNO, FTO), it is possible to carry out direct deposition of probes having a hydrophilic group such as $PO_3^-$ (cf ref) as is the case with nucleic acids.

The parts of the electrodes which have not received a probe graft have to be isolated by an encapsulation process. As an example, a film of poly-pyrrole may be used. The film is produced by placing the grafted electrodes under tension in the presence of a solution of pyrrole. The pyrrole polymerizes spontaneously under the action of the current and isolates the free parts of the electrodes. After grafting the probes, the electrodes may also be saturated by a monomeric oligonucleotide (for example polyA) which cannot hybridize with the targets.

The Invention Concerns a Process for Binding a Nucleic Acid Polymer to an ITO Electrode by Direct Adsorption.

When the device comprises two networks of capillaries, it allows the mixture to be analyzed to more through the set of micro-columns. The corresponding targets are specifically retained on each micro-column. They are then eluted, i.e. detached from the molecular probes to which they were specifically bound, then migrate towards one or more detectors via the network of capillaries at the micro-column outlet.

Because of the large number of micro-columns, it will readily be understood that it may be advantageous, for sequential analysis of the targets, to be able to separately control elution and/or migration at each micro-column or at least distinct groups of micro-columns, for example row by row in the case of a matrix of N*P micro-columns, as described in a preferred example.

The network of capillaries are, for example, hollow or molded in materials such as silica, plastics (for example Plexiglass) using acid erosion techniques for silica or machining laser for plastics, all of which are known to the skilled person.

In a preferred embodiment, each network of capillaries is hollowed into the thickness of a plate of a suitable material. The device then comprises the matrix of micro-columns and the two plates onto which the network of capillaries have been hollowed, joined to each of the faces of the matrix (Kuo et al—Anal Chem, 2003; 75(10), p 2224-2230; Kuo et al, Anal Chem, 2003; 75(8), p 1861-1867).

In a specific embodiment, the device of the invention as described above is characterized in that it comprises means for controlling, at one or more specific micro-columns of the matrix, elution of molecular targets and/or their migration towards a detector and/or their retention in the micro-columns after elution.

The term "elution" means the operation consisting of breaking the specific bond established between the target and the probe.

Within the context of the invention, the term "elution control" and/or "target migration" in specific micro-columns means that the device can select micro-columns for which the targets will be eluted or will migrate towards the detector, the other targets not being eluted or being retained in the micro-columns despite the possible presence of a flow traversing said micro-columns.

Provided that it is then possible to separately analyze the targets eluted from each micro-column or a group of micro-columns using the same analysis device, the device of this embodiment can in particular limit the number of detectors used.

In a particular embodiment, when the molecular targets are charged molecules, for example nucleic acids, it is possible to control elution and/or migration of these targets by applying an electric field, for example by means of a set of electrodes disposed in contact with each micro-column and at the outlet from each micro-column. The electrodes in each cell may be independent of each other (cell by cell multiplexing) or organized into groups of electrodes each forming a potential unit for a group of cells.

Thus, in a specific embodiment, the device of the invention comprises an electrode, termed the cell electrode or median electrode, disposed in contact with each micro-column, preferably median to the micro-column, and a second electrode, termed the distal electrode, disposed at the outlet from each micro-column, to control elution of molecular targets retained in one or more specific micro-columns and/or their migration towards the detector or their retention in the micro-columns after elution.

The cell electrodes are disposed so as to retain charged molecules in the micro-columns after elution by electrical interactions then to allow their selective migration. When the cells are tubular in shape they are, for example, disposed in contact with the side walls of the cells.

Provided that the device allows separate elution and/or migration of molecular targets towards a detector, the device may comprise a network of suitable capillaries which allow the molecular targets to converge at the micro-column outlet towards a restricted number of detectors, or even to a single detector.

In a preferred embodiment, the device of the invention is characterized in that the first network of capillaries serving as the inlet to the micro-columns comprises a first transverse capillary into which the complex mixture is introduced, hereinafter termed the upper transverse channel, preferably with a diameter in the range 2 to 1000 µm, connected to a set of capillaries acting as the micro-columns of the matrix, and in that the second network of capillaries serving as the outlet from the micro-columns constitutes a set of capillaries connecting the micro-columns to one or more transverse capillaries, termed lower transverse channels, preferably with a diameter in the range 2 to 1000 µm, the latter being connected to one or more detectors.

The lower and upper transverse channels are preferably each connected to an electrode, allowing a potential difference to be applied between the location at which the complex mixture to be analyzed is introduced and the detector, to ensure migration of charged molecules into the whole of the device, in particular nucleic acids contained in the complex mixture to be analyzed by electrophoresis.

In a particularly preferred embodiment, the device of the invention is characterized in that the matrix of micro-columns comprises N rows and P columns of micro-columns disposed in the same plane and in that it comprises means for controlling elution of molecular targets retained on the micro-columns of a specific row and/or their migration towards the detector and/or their retention in the micro-columns after elution, and in that the length of each capillary of the second network is selected so that the distance between the outlet from a micro-column and the lower transverse channel is different from one capillary of the second network to another, preferably increasing or decreasing from the capillary connecting the first micro-column of a row to the capillary connecting the last micro-column of said row, such that the residence time for molecular targets at the outlet from the micro-column to the detector are different for each micro-column of the same row.

As an example, to obtain different migration times for the targets from each micro-column of the same row, the network of capillaries connecting each micro-column to the lower transverse channel may comprise P parallel capillaries, each capillary connecting the P micro-columns of the same row of the matrix to the lower transverse channel and forming an angle with said lower transverse channel which is other than 90°. To further increase the delay, the parts of the capillaries located between the last rows of cells and the transverse channel follow non linear trajectories.

The migration times for the various targets allow the micro-column from which the targets derive to be identified and thus allow the target in question to be identified by the molecular probe contained in the micro-column. The diameter of the capillaries and the density of any gels used inside them are thus selected so as not to discriminate migrating molecules by size, the migration time depending solely on the trajectory which is followed. However, the gel density may optionally be selected to carry out chromatography by capillary electrophoresis. Molecules with different sizes or with a slight sequence polymorphism such that they hybridize to the same probe are thereby delayed to different extents by an appropriate gel during their migration.

Preferably, the lower transverse channel and the various portions of the second capillary network with different distances are filled with gel. For this reason, targets will migrate rapidly to different portions of the capillaries of the second network where they will be chromatographed.

To control elution and/or migration of targets for each row of micro-columns of the device, the set of P micro-columns of one row may be connected to the same electrode, the device of the invention then comprising N row electrodes (cell row electrodes), preferably median to micro-columns, and a second series of electrodes, parallel to the row electrodes (distal row electrodes), connecting the set of P capillaries at the outlet from the micro-columns of the same row.

A network of cell row electrodes or median row electrodes is thus obtained: one electrode per row of the micro-column matrix. These electrodes, in addition to allowing nano-manipulation of targets in each of the cells, can catalyze probe binding, such as probes bound to pyrrole which bind to each electrode under the effect of an electric field. The second set of distal row electrodes, a mirror image of the cell row electrodes, is disposed at the outlet from the cells of the micro-column matrix. The pairs of row electrodes define potential units of the matrix of N*P micro-columns. These pairs of electrodes can apply the desired potential to each row of micro-columns.

In a preferred embodiment of the device, the first and second network of capillaries are located in planes parallel to the plane of the micro-column matrix, preferably respectively above and below the plane formed by the matrix of micro-columns, and the first network of capillaries, termed the upper network, comprises N parallel capillaries, each capillary connecting the upper transverse channel to P micro-columns of a single row of the matrix, and the second network of capillaries, termed the lower network, comprises P parallel capillaries, each capillary connecting the N micro-columns of one column of the matrix to the lower transverse channel, the angle formed between the two networks of capillaries, lower and upper, being other than 0°, preferably 90°. For this reason, each capillary of the upper network is connected to all capillaries of the lower network via a row of P cells of the micro-column matrix. Reciprocally, each capillary of the lower network is connected to all capillaries of the upper network via a column of N cells of the micro-column matrix.

In a particular embodiment comprising such a matrix of N*P micro-columns, the ends of the capillaries of the upper network opposite to an upper transverse channel preferably stop at the last connection with the $P^{th}$ and last micro-columns of the rows of the micro-column matrix, and the ends of the capillaries of the lower network opposite to a lower transverse channel preferably stop at the last connection with the $N^{th}$ and last cells of the columns of the micro-columns of the micro-column matrix.

In a further embodiment, the end of the capillaries of the lower network of capillaries opposite to the transverse channel is connected to a second transverse capillary (secondary lower transverse channel), said channel allowing a flow to be established between the two networks of lower and upper capillaries through the micro-column matrix, this allowing migration into the lower capillary network to be accelerated and more finely controlled. If the lower principal transverse channel is filled with a gel to carry out capillary microelectrophoresis, it is still possible to establish a closed loop flow between the upper transverse channel and the secondary lower transverse channel.

In general, the capillary networks may be filled with gel such as a polyacrylamide gel or any other gel allowing the stream to be adjusted and allowing diffusion of molecules during their migration to be controlled, in particular liquid gels used for capillary electrophoresis.

In a particular embodiment of the device containing a matrix of N*P micro-columns, the upper and lower transverse channels are provided with a piston, which may or may not be threaded, allowing the number of rows of micro-columns through which the flow may pass to be selected. As it draws back, the piston mobilizes more and more rows of the micro-columns of the matrix.

It may be possible to mobilize the rows of the micro-column one by one by producing a hollow piston provided with a slot.

In a specific embodiment, movement of the targets during the hybridization phase is carried out without a flow, by establishing an alternating electric field between the electrodes of the upper and lower transverse channels and the successive row electrodes. This field allows the non-hybridized targets to be mixed regularly to homogenize the hybridization solution. Further, by adjusting the electric field strength, it is possible to control the hybridization specificity (Cluzel P, 1996, Science, Vol 2071 (5250) pp 792-794).

A simpler alternative to using a double network of superimposed capillaries consists of using a single network and a set of row electrode pairs to constitute the device of the invention.

The device is then in the form of a matrix of probes organized into spots (corresponding to a hybridization unit) where each spot is constituted by one type of molecular probe, for example of the nucleic acid polymer type the sequence of which is specific to a gene (for proteins, it may be a type of antibody or a particular ligand). Each row of spots of the matrix is deposited on a surface of gold or ITO (or any other suitable metal or alloy) defining an electrode, the whole of the matrix then being constituted by n electrodes corresponding to the number n of rows, each row electrode comprising. P spots of grafted probes (cf FIG. 7). The electrodes are etched as a thin layer onto an insulating material such as glass, Kapton, aluminum oxide, etc (see diagram).

A second set of electrodes, a mirror image of the first, is produced, but this time the electrodes are not grafted with the probes; these electrodes are termed non-functionalized. The two sets of electrodes are disposed face-to-face either side of a network of P parallel capillaries, so that one set of electrodes is above and the other is below it (FIGS. 8 and 9). The first set of functionalized electrodes has grafted probe electrodes organized into spots, each probe being capable of retaining a specific molecular target when it is present in the complex mixture, by specific probe/target binding. The second set of electrodes has non-functionalized electrodes. In a specific example, the set of functionalized electrodes is located above the network of capillaries and the set of non-functionalized electrodes is located below the network of capillaries. Each capillary is perpendicular to n electrodes of the set of functionalized electrodes and to n electrodes of the non-functionalized set of electrodes (FIG. 9, 10, 11). The construction is produced so that the first spot of the n functionalized electrodes is in the first capillary of the network of capillaries, the second spot of the n functionalized electrodes is in the second capillary of the network of capillaries and so on (FIG. 11). A electrode pair is constituted by a grafted electrode of probes organized into spots above the network of capillaries and a facing non-functionalized electrode below the network of capillaries. The electrodes may be very thin to allow detection by SPR. At each end of the network of capillaries, the capillaries converge towards a circular reservoir. The reservoir comprises an electrode (reservoir electrode) in the same plane as that of the set of functionalized electrodes (FIG. 11). In a specific example, this electrode is circular. In a specific example, this electrode is located in the centre of the ceiling of each reservoir. The set of functionalized electrodes (grafted electrodes of probes) is completed by two supplemental connection electrodes: a first curved electrode is located between the first reservoir electrode and the first functionalized electrode, and a second curved, electrode is located between the second electrode reservoir and the last functionalized electrode. The connection electrode is curved; its curvature is defined so that the distances between the connection electrode and the centre of the reservoir (reservoir electrode) are identical at any point on the electrode.

The first and second supplemental connection electrodes are located respectively between the first reservoir electrode and the first functionalized electrode, and between the second reservoir electrode and the last functionalized electrode, so that the shortest distances between the connection electrode and the reservoir electrode are identical at any point on the electrodes.

The above description of the device of the invention comprising a double network of capillaries, the constituent elements of the network such as capillaries, electrodes, detectors, etc, can be transposed to the preparation of a device comprising a single network, provided that it is compatible with the function of said single network device, and adapted if necessary to this structure.

In analogous manner, the description of the molecules to be analyzed and the probes used, as well as their preparation and the features of their use and detection, may be transposed to the preparation of a device comprising a single network, provided that it is compatible with the function of said single network device and adapted if necessary to said structure.

The principle of the function of the device comprising a single network of capillaries uses active hybridization (ha) and may be described as follows:

1/the sample (FIG. 12) to be analyzed is introduced into the first reservoir. An electric potential is applied between the first connection electrode (positive) and the electrode of the first reservoir (negative) when the molecules analyzed are nucleic acids. The potential may alternatively be inverted in the case of protein analysis. The description below concerns the function for nucleic acids. The molecules to be analyzed migrate in an equimolar manner in each of the capillaries and are concentrated at the connection electrode.

2/The potential between the reservoir electrode and the connection electrode is then cut and an electric potential is applied between the functionalized first electrode (+) and the connection electrode (−). The molecules of each capillary then migrate to the functionalized first electrode where the targets complementary to the spots of the first electrode (one spot per capillary) may hybridize (hybridization is accelerated by the electric field). The concentration at each spot is a maximum (it only depends on the number of capillaries and no longer on the total volume of the channels).

3/To control the targets at the spot, the second row electrode (non-functionalized) may be taken to a negative potential; a (−+−) charge distribution is obtained where the +charge is centered on the first spot of each capillary. To improve hybridization, the electric potentials may be discontinued, the time lapse without potential corresponding to a relaxation time, during which the targets may hybridize without constraint. To increase mixing of the targets to be analyzed and thus favor hybridization of targets present in small numbers, during the relaxation time a discontinuous and alternating potential may be established between the first electrode pair above and below the network of capillaries (this further increases the hybridization specificity).

Once the targets are targets at the first row of spots, the electric potentials are offset by one row. If 0 is the position of the connection electrode and 1, 2, 3 are respectively the positions of the first, second and third functionalized electrodes grafted to the probes, the applied electric potential sequence may be described as: 4/the second functionalized electrode is taken to a positive potential; the charge distribution is (0−, 1+, 2+) (optionally, the third electrode is at a negative potential) with a charge distribution (0−, 1+, 2+, 3−);

5/The first functionalized electrode is taken to a negative potential; the charge distribution is (0−, 1−, 2+), optionally (0−, 1−, 2+, 3−);

6/the connection electrode is taken to 0 for a charge distribution (1−, 2+), optionally (1−, 2+, 1−);

7/discontinuous and alternating electric potential between the 2 functionalized electrode and the 2 non-functionalized electrodes.

The set of probes not hybridized to the first row of spots will migrate to the second row of spots. All of the migration, relaxation and mixing sequences (points 4 to 6) are applied step by step to hybridize all of the spots of all of the rows which have complementary targets in the analyzed sample. Once they reach the second reservoir, the targets which have migrated in different capillaries are mixed again. It is then possible, in a variation, to carry out sequences of electric potential in the other direction to cover the network of capillaries in the reverse direction. The to-ing and fro-ing of the targets between the two reservoirs through the capillaries can increase the detection sensitivity of the device.

Several detection possibilities may be envisaged to quantify the targets hybridized in the device with a single network of capillaries, as described above for the device with a double network of capillaries.

Using SPR:
- the targets may be quantified directly on the network of functionalized electrodes. A trihedral prism is fitted to the back of each row electrode of the network of functionalized electrodes to be able to carry out the SPR measurement (see description on SPR detection).
- to reduce problems with background noise and detection sensitivity, the SPR measurement may be carried out on the set of non-functionalized electrodes where the face opposite to the capillaries of each electrode is coupled to a trihedral prism (see SPR section). In this detection process, the set of functionalized electrodes may be coupled to a structure where each spot is walled off and delimited by a small cell (FIG. 13). Each cell is a small cup, the base of which is constituted by the functionalized electrode and which opens into the capillary facing the non-functionalized electrode (cell open only to one side of a capillary of the network of capillaries). The walls of the cells prevent the targets of one spot mixing with that of another during migration of one of the targets between the functionalized, electrode and the non-functionalized electrode.

In the context of using cells open only on one side and a single network of capillaries, it is possible to adapt a transverse channel to the system of capillaries and a system for delaying migration (as described for the lower network of capillaries of the double network (see section)). In the context of using a single capillary network, it is possible to do away with the second reservoir and replace it with a channel transverse to the capillary system and a migration delay system (FIG. 14). Hence, the same types of detection described for the system having two superimposed networks of capillaries are applicable to the simplified system.

In this configuration, the first connection electrode is curved so that the distances between the connection electrode and the centre of the reservoir are identical at any point of the electrode, and in that the second connection electrode is not curved. This electrode acts as a barrier which cannot be penetrated by probes during hybridization, then the detection step allows the targets to be directed towards the delay system using potentials established by the target electrode and the connection electrode.

If the element has an acute angle with respect to the transverse channel, the delay effect is amplified.

Using fluorescence:
- if the targets are labeled with a fluorescence marker, it is possible to read the hybridized targets directly using a scanner over the set of functionalized electrodes. In similar manner to the use of fluorescence coupled with SPR (excitation of fluorescence molecules by the damped wave of SPR) may be used.
- without labeling the targets, the amount of probe/target complexes may be evaluated using fluorescence ligands for the target or the complex. For DNA arrays, acridins may be cited, in particular acridin orange which is an intercalating agent for positively charged DNA. Acridin orange can label single or double strand DNA differently, the free molecules will be eliminated due to the action of the electric fields produced by the systems of electrodes. The set of measurements may be made during hybridization reactions or complexing reactions by dint of the set of electrodes which can manipulate the set of charged molecules. Using this approach, it is possible to evaluate the number of molecules of probes composing the spot and the number of targets which have hybridized; these two measurements allow the real concentrations of the targets in solution to be determined.

To prevent unwanted fluorescence from electrodes, the connections may be produced with ITO type alloys which are transparent in the visible spectrum (indium oxide and tin oxide or any other equivalent alloy, such as . . . ). Since these alloys are highly electrophilic, they must undergo a chemical isolation procedure as described in the chemical isolation section.

In a particular construction of the device of the invention, the probes may be deposited between the electrodes of a set of functionalized electrodes (FIG. 7).

In the context of using a double network of capillaries, the device of the invention comprises one or more detector(s) appropriate for separately collecting molecular targets and/or to separately analyze molecular targets, hereinafter termed the detector(s).

In preferred embodiments, the detector is connected to the outlet of a lower transverse channel connecting the capillaries of the second network. In the text below, a device comprising a detector and a lower transverse channel connecting the set of capillaries of the second network will be described in detail. Clearly, other variations may be envisaged; in particular, several detectors may be used, each detector being connected to the outlet from a lower transverse channel connecting part of the capillaries of the second network.

Any detection system may be adapted to the outlet from the second network of capillaries, in particular as a function of the type of labeling used to differentiate the molecular targets deriving, for example, from the various samples.

By way of example, if the targets can be located by fluorescence, in particular after labeling with a fluorescent probe, detection may be carried out using a spectrophotometer allowing excitation and acquisition of the fluorescence from labeled molecules or the intrinsic fluorescence of the molecules being studied. To this end, in a specific embodiment, it is possible to add a capillary hollowed into a quartz crystal or any other transparent material allowing excitation and acquisition of fluorescence (for example a plastic) to the outlet from a lower transverse channel. The fluorescence is excited and read during passage through the quartz capillary. The natural fluorescence of the molecules being studied may be used for detection. Similarly, crystals of NaCl or KCl may be used to carry out infrared spectrometric studies or Raman spectroscopic studies.

Alternatively, target detection and quantification employs paramagnetic resonance or electronic resonance if the targets are labeled by a paramagnetic marker.

When detection is carried out by SPR, the distal row electrodes or lower row electrodes are constituted by a sheet of gold (or another free electron metal) several tens of μm thick. The outer face (opposite to the channels) of each distal electrode is connected to one of the three faces of a prism (glass, quartz, plastic or any other transparent material which may be suitable for SPR). The prism is constituted by a trihedron one of the three rectangular faces of which is coupled to the outer face of a distal row electrode, the length of the trihedron corresponding to that of the electrode (FIG. 15).

After target hybridization, the micro-column circuit is rinsed and purged of all non-hybridized targets, the hybridized targets are retained in each cell or each spot for the simplified design. The system is placed under tension so that at each pair of row electrodes, the potential is positive at the median electrode and negative at the distal electrode respectively in the design of functionalized and non-functionalized electrodes. For the sake of the description, the functionalized electrode will be the same as the median electrode and the non-functionalized electrode will be the same as the distal electrode. For protein arrays, antibody arrays or molecular receptor arrays, the potentials are adapted to the function of the charge of the molecules being studied. A chaotropic agent capable of destroying the capable of destroying the probe-target complex is introduced into the medium. The probes separate from the targets, but are retained in each cell or spot by the negative charge of the median electrode (FIG. 16). The potential at the first electrode pair is reversed so that it is positive at the distal electrode, and negative at the median electrode (FIG. 16). The targets of the row of cells or spots dependant on the electrode pair will migrate into the network of capillaries to come to the distal electrode perpendicular to the network of capillaries (lower network for the system of two superimposed networks), so that the probes of each cell or spot are found in a different capillary.

The invention also concerns an SPR analysis method comprising:
  hybridization of targets on an electrode;
  dehybridization by a chaotropic agent;
  maintaining the targets by an electric potential;
  reversing the potential to migrate the targets to a non-functionalized electrode;
  measuring the SPR on the non-functionalized electrode.

The SPR measurement is made by reflecting light onto the outer face of the distal electrode through prisms disposed on each electrode. It is possible to estimate the dissociation constant by observing the rate at which the measured SPR signal varies with time. By applying an alternating current between a pair of row electrodes, it is possible to measure the association and dissociation probe/target constants. In the particular case of experiments made without denaturing agent, the variations in local concentration induced by the electric field can produce associations and dissociations of probes and targets.

The current applied to the electrodes may disturb the SPR signal. To limit this perturbation, the field applied between the pair of row electrodes may be discontinuous. If the SPR measurement is then only made during the field interruption phases, then we have pulse SPR measurements coupled to the frequency of the electrical field. It is possible to determine the diffusion coefficient of the molecule by analyzing the rate of variations of the SPR signals as a function of the electrical field interruption time between the pair of row electrodes. The same operations are repeated for each pair of row electrodes.

Because the metal surface is not functionalized, the targets may come into contact directly with the metal, which thereby increases the detection sensitivity. Further, the electric field can maximize the concentration of targets at the surface of the metal, which further increases the detection sensitivity. Since SPR detection is dependent on mass, the heavier the molecules to be detected, the more efficient is the detection. An increase in the mass of the molecules can thus reduce the detection threshold. Using targets in which the atoms have been replaced by heavy isotopes can increase the molecular mass and thus reduce the detection threshold.

In the context of the alternative corresponding to the use of a single network of capillaries, it is possible to directly measure the impedance of molecules which bind to a target by direct electrical detection.

In addition to its role of manipulating probes and targets by an electric field, the system of electrodes implanted in the arrays allows the impedance of molecules which bind to a target to be measured directly. To reach a high spot density, $10^3$ to $10^6$ on a surface of less than $20\,cm^2$, a system of crossed electrodes is produced. The system is composed of two sets of superimposed electrodes located in two different planes below and above a matrix of spots of probes. The direction of the non-functionalized set electrodes is perpendicular to that of the electrode of the functionalized set (FIG. 17). The spots are implanted, for example, on electrodes of the functionalized set at each intersection of the functionalized electrodes and of the projection into the upper plane of the electrodes of the non-functionalized set. Fixing the probes depends on the nature of the electrodes and the nature of the probe molecules (see section on implantation of probes and isolation of electrodes). In the context of DNA molecules, it is desirable to stress the conformation of the molecules as much as possible to minimize measurement problems due to the curvature of the DNA and intra-molecular hybridization, which cause variations in the impedance which are of the same order as for hybridization. A solution to stressing DNA consists of adsorbing onto the electrode by molecular combing. The molecules stretched onto the electrode can no longer bend or hybridize with themselves; in contrast, they keep the faculty of hybridizing with a complementary sequence in solution. Another solution consists of stretching the probe molecule between an electrode of the functionalized set and an electrode of the non-functionalized set, by fixing it to the electrodes by its ends. The oligonucleotide probes used are functionalized at the two ends, 5' and 3'. The 5' function is different from that at the 3' end. The two types of function have a different activation and/or catalysis. It is, for example, selected from Hs, $NH_2$ functions at 5' with a chemical or light activation and a pyrrole function at 3' with electrical catalysis. The distance between the sets of functionalized and non-functionalized electrodes is selected so that the molecules are stretched without having to adopt a particular curvature or producing intramolecular hybridization. An alternative consists of functionalizing the 5' end of the probe to graft it to the functionalized electrode and to add a short sequence (10 to 20 bases) at the 3' end. The 3' sequence is specifically selected to that there is no hybridization with the targets. A sequence complementary to the 3' adjunct is grafted to the facing non-functionalized electrode. The probes are fixed to the electrode of the functionalized set by their 5' end by means of a chemical bond and to the non-functionalized electrode via the 3' end by means of a duplex of 10 to 20 base pairs formed between the adjunct and its complementary sequence grafted to the electrode. The probes are thus stretched between the two electrodes, which minimizes intramolecular hybridizations and the curvature.

The electrode array with the grafted probes may be hybridized passively by simple diffusion of targets at each spot, as is currently carried out with bioarrays. However, active hybridization is preferred using the method described above. To this end, a network of capillaries and two reservoirs similar to those described in the preceding section are disposed between the functionalized and non-functionalized set of electrodes. Two electrodes from reservoirs and two connection electrodes are added to the set of functionalized electrodes (see diagram). Once the array has been hybridized, the variation in the impedance of each spot allows the quantity of bound targets to be determined. The intersection between a functionalized electrode and the projection (into the upper plane) of a non-functionalized electrode is unique and corresponds to a single spot. The impedance measurement is carried out spot by spot by applying, in succession, an electric potential difference and an electric current to all possible pairs of electrodes formed by a non-functionalized electrode and a functionalized electrode.

The perpendicular disposition between the two sets of superimposed electrodes, can in theory allow the measurement to be made. However, using an alternating or discontinuous current and the fact that one electrode connects several spots causes problems with unwanted capacitance, which perturbs the measurement. It becomes difficult if not impossible to measure the current and the electrical voltages properly to define the impedance of each spot. To overcome this problem, switches must be introduced to allow a spot-to-spot tension and current to be established. To produce switches compatible with the dimensions of bioarrays, the set of functionalized electrodes (or the non-functionalized set) is replaced by a grid of electrodes in one plane, constituted by a first (horizontal) set of electrodes isolated from and perpendicular to a second set of electrodes of the first set (vertical). The mesh of the grid defines a space in which a small electrode is disposed with 10 to 500 µm sides (spot electrode), depending on the size of the grid. At each mesh of the grid one or two field effect transistors are disposed so that the transistor gate is connected to a horizontal electrode of one side of the mesh, the inlet terminal (source) of the transistor to the vertical electrode of one side of the mesh and the outlet terminal (drain) of the transistor to the spot electrode.

In summary, we obtain a grid the meshes of which, defined by the horizontal and vertical electrodes, are occupied by small spot electrodes. The spot electrodes are connected to two of the four sides of the mesh by one or two field effect transistors (FIG. 17, 18). The molecular probes are grafted to each spot electrode. The electrodes of a non-functionalized set are disposed facing each column of "spot electrodes" and parallel to the vertical electrodes of the functionalized grid. Each electrode of the non-functionalized set is earthed. The set of non-functionalized electrodes may be replaced by a single earthed plate.

When the impedance is measured with an intermittent current (the current is always in the same direction), a single transistor per "spot electrode" is necessary in order to act as a switch. By placing the horizontal electrodes under tension, the gates of all of the transistors are supplied, which cuts the current between the input and drain of all transistors, and thus the electrodes spot are isolated. By cutting off the current at a single horizontal electrode and applying the current and an intermittent electric field to a single vertical electrode, only the transistor at the intersection of the two electrodes allows current to pass between its input and its drain. A single spot is placed under tension; the variation in the impedance at the spot electrode may be determined without interference from other spots.

When the impedance is determined with an alternating current (the current moves in both directions), the spot electrode has to be supplied regardless of the direction of the current. Thus, two field effect transistors must be disposed in the mesh, with opposing characteristics, i.e. when the tension at the gates of the transistors is zero or negative, the current can pass between the input and drain in one direction for the first transistor and in the other direction for the second transistor. Regardless of the direction of the current, the spot electrode is supplied. It would be advantageous to introduce transistors allowing current to pass in the two directions between the input and the drain, such as in "nmos" or "pmos" type transistors, but such transistors have an additional terminal and thus require one horizontal electrode per mesh to make the connection, which limits miniaturization.

It is possible to carry out mixed detection of fluorescence and impedance or fluorescence alone (the electrodes are then only used to control hybridization in accordance with the above description of active hybridization (ha)). In order not to ruin the fluorescence emitted by the probes or targets, the set of circuits and electrodes may be produced using a transparent alloy such as ITO. In the context of detection by fluorescence for nucleic acids, an alternative to labeling targets by a chromophore consists of using a fluorescent intercalating agent for the nucleic acids. Acridins are good candidates and in particular acridin orange, which has the feature of fluorescing in a different manner when it is associated with single strand DNA or a DNA/DNA duplex. Further, acridin orange is positively charged, which means it can move in an electric field. The density of the probes in each spot is determined by labeling with acridin orange and measuring the fluorescence emitted, the various applied electric fields allowing acridin orange molecules not fixed to DNA probes to be eliminated. The sequence of application of electric fields is similar to that described in the "ha" section above, but the direction of the fields is adapted to the charge of the molecule which is to be displaced. Once the targets have been introduced onto the array, measurement of the fluorescence relative to the formation of the DNA/DNA complex allows the concentration of each target type to be determined by comparing it to the fluorescence of the probes. This method enables dynamic hybridization measurements to be made and allows the dissociation constant (kd) and association constant (ka) to be determined between the targets and the probes. Measurement of kd and ka for a target may be compared with the measurements obtained for the native sequence, which means that polymorphism may be demonstrated. More generally, by carrying out a mixed measurement, it is possible to demonstrate mispairing of the probe for the target, for example using an intercalating agent and a fluorescent marker for targets with a chromophore, or an impedance measurement and an intercalating agent, etc.

In particular, a detector used in the device of the invention is a mass spectrometer. The mass spectrometer can, at the same time, inform the operator as to the number of target molecules and the nature of these molecules (molecular weight and, under certain conditions, their formulae). The device may, for example, comprise a lower transverse channel contiguous with ElectroSpray ionization (ESI) (Kebarle et al, Anal Chem; 1993; 65 (22); p 972-986) of a mass spectrometer. Preferably, the lower transverse channel is connected to the detector via a piezoelectric or thermal pipette which allows regular injection into the ElectroSpray. Any improvement to ESI can be adapted, such as microspray (micro ESI), nano spray (nano ESI), pico spray (pico ESI) (Smith et al, T Matsio et al, Editors 1995, John Wiley & Son: Baffins Lane, Chichester, W Sussex, UK, p 41-74; Emmett et al, J Am Soc, Mass Spectrum 1994, 5, p 605-613; Valaskovic et al, Anal Chem, 1995, 67 (20), p 3802-3805). Other types of detector, such as orthogonal acceleration time of flight or quadripole analyzers (aoTOF or QTOF) (Chemushevich et al—Proceedings of the 43$^{rd}$ ASMS Conference on MS and Allied Topics, 1995, Atlanta, Ga.; Sanzone G—Rev Sci Instrum, 1970, 41 (5) p 741), may be used in the device of the invention.

Data regarding the mass and charge of molecular ions and the number of molecular ions allow the nature and the number of each type of molecular target specifically retained in a given micro-column to be deduced. The formula for the molecules specifically linked to probes at each micro-column may in particular be deduced by specific labeling of the targets and the decomposition of the molecules during spectrum acquisition using the MS/MS method (Chemushevich et al, Proceedings of the 43$^{rd}$ ASMA conference on MS and allied topics, 1995, Atlanta, Ga.). In a particular embodiment, joint fluorescence detection and mass spectrometry may also be envisaged, by mounting the quartz capillary allowing fluorescence analysis and the ElectroSpray in tandem. In the same manner, a plurality of different types of detectors or analyzers may be mounted in tandem.

In a specific embodiment of the device of the invention, it is possible to analyze various transcriptomes of various samples in parallel.

In this particular embodiment of the device, the device comprises nucleic acids (immobilized in cells or on particles) constituted by a set of nucleic acids representative of a transcriptome.

The term "representative of a transcriptome" means that the nucleic acids immobilized in the cell have identical or complementary sequences or specifically hybridize under stringent conditions with messenger RNAs, transcription products of nucleic acid sequences from a genome of a given cell or a set of cells, and are in proportions equivalent to those of the transcription products obtained under particular conditions for said cell or set of cells.

Methods for preparing nucleic acids representative of a transcriptome are described in the examples below.

Preferably, the set of nucleic acids representative of a transcriptome is immobilized on particles, said particles being immobilized in micro-columns by suitable means. Using the method described in Example 3 below, the device can then analyze the various transcriptomes in parallel.

In particular, the invention envisages particles per se comprising a set of immobilized nucleic acids representative of a transcriptome.

It also concerns a set of nucleic acid molecules selected according to the criteria defined in Example 3. The set of nucleic acid molecules is in particular used with the micro-columns array comprising sets of nucleic acids representative of transcriptomes in each micro-column.

In another embodiment, the device of the invention is characterized in that the molecular probes are peptides or polypeptides, preferably antibodies or their antigen-binding fragments.

The invention naturally envisages uses of the device in detecting and/or assaying specific RNA and/or DNA molecules contained in a biological sample, in particular in a cellular extract, the molecular probes being selected so that they hybridize specifically with a type of RNA or DNA contained in the biological sample. The use of such a device can in particular allow a comparative analysis of specific RNA and/or DNA molecules contained in at least two biological samples using the method described in Example 4, for example.

By appropriate selection of several probes per gene, for example one specific probe per exon, the probes can be quantified to provide a specific signature of the splicing of a gene.

The invention also concerns a method for separating and analyzing molecular targets in solution in a complex mixture, said method comprising:

a. introducing a complex mixture containing molecular targets to be separated into a device in accordance with the invention as described above;
b. moving the complex mixture through the micro-column matrix of the device under conditions appropriate for allowing targets to bind specifically to the probes of the micro-columns;
c. eluting targets specifically retained on the micro-column probes;
d. moving targets eluted from the micro-columns towards a detector;
e. recovering and/or analyzing each target using a detector.

In a specific embodiment, the invention pertains to a method for comparative analysis of at least two populations of specific DNA or RNA molecules contained in two biological samples, said method comprising:

a. labeling DNA or RNA molecules derived from a first sample, for example with a heavy isotope, to provide mass differentiation of a labeled DNA or RNA molecule contained in the first sample from that of a DNA or RNA molecule with an identical structure but not labeled contained in a second sample;
b. equimolar mixing of two DNA or RNA populations to be compared;
c. introducing an equimolar mixture into a suitable device of the invention comprising a detector constituted by a mass spectrometer;
d. moving the equimolar mixture through the micro-column matrix of the device under conditions appropriate to allow specific binding of the targets to the micro-column probes;
e. eluting targets specifically retained on the probes of micro-columns;
f. moving targets eluted from micro-columns towards a mass spectrometer;
g. detecting and/or assaying each target, labeled or not labeled, using a mass spectrometer.

In a particular implementation of this method, the device selected to carry it out is constituted in particular by pairs of row electrodes as described above, to control elution and/or migration of targets eluted at each row of the micro-columns. In this case, a preferred implementation of the method comprises the following steps:

a. introducing a complex mixture containing DNA and/or RNA molecules to be separated into the appropriate micro-column device of the invention;
b. moving the complex mixture through the micro-column matrix of the device under conditions appropriate to allow specific binding of targets to the micro-column probes, preferably in a closed circuit;
c. if appropriate, moving a rinsing solution through the micro-column matrix to eliminate non-hybridized or not specifically hybridized molecules, in an open circuit;
d. applying an electric potential difference between the pairs of row electrodes of the micro-columns which is positive at the cell electrodes and negative at the distal electrodes, and applying an electric potential difference between the pairs of transverse channel electrodes, negative at the lower transverse channel, and positive at the upper transverse channel, so that the DNA or RNA molecules are retained in each micro-column after denaturing in step e;
e. moving a denaturing solution through one or more rows of the micro-column matrix under conditions allowing denaturing of the probe/target complexes and thus elution of DNA or RNA molecules;

f. reversing or suppressing the electric differential applied to the row electrode pair of a row of micro-columns of the matrix;
g. moving denatured targets from the micro-columns of a row of the matrix towards a detector;
h. recovering and/or analyzing each target using a detector.

A preferred alternative to the method described above allows the steps for denaturing and migrating the molecular targets to be carried out using only an electric field. Such a method is characterized in that it comprises:
a. introducing a complex mixture containing DNA and/or RNA molecules to be separated into an appropriate device in accordance with the invention;
b. moving the complex mixture through the micro-column matrix of the device under conditions appropriate for allowing specific binding of the targets to the micro-column probes, preferably in a closed circuit, if necessary under the effect of an alternating electric field between the electrodes of the transverse channels and the successive row electrodes, as described above;
c. if necessary, moving a rinsing solution through the micro-column matrix to eliminate non-hybridized or not specifically hybridized molecules, in an open circuit;
d. connecting the lower transverse channel to a first reservoir containing a denaturing solution comprising negative ions capable of migrating in an electric field and connecting the upper transverse channel to a second reservoir comprising a denaturing solution comprising the same negative ions.
e. applying a negative electric potential to the lower and upper transverse channels and the distal row electrodes, and a positive electric potential to the cell row electrodes, so that the negative ions of the solution migrate towards the positively charged micro-columns and cause the molecular targets to denature, the thus denatured molecular targets being immobilized in the micro-columns due to the negative electric potential at the distal row electrodes;
f. applying an electric potential difference between the pairs of transverse channel electrodes, which is negative at the upper transverse channel and positive at the lower second transverse channel;
g. reversing or suppressing the electric differential applied to the row electrode pair of a micro-column row of the matrix to allow the denatured targets to migrate by electrophoresis from the micro-columns of a row of the matrix towards a detector;
h. recovering and/or analyzing each target using a detector.

The invention also pertains to a method comprising:
a. constituting a device of the invention in which each micro-column contains RNA or DNA targets in proportions representative of a transcriptome;
b. introducing a stoichiometric mixture of probes specifically complementary to the RNA or DNA targets immobilized in each micro-column of the matrix, each specific probe of a target having a molecular weight which differs from the other probes and is thus distinguishable from the others in a mass spectrometer;
c. moving the mixture of probes through the micro-column matrix of the device under conditions appropriate to allow specific binding of the probes to the targets immobilized on the micro-columns;
d. eluting probes specifically retained on the targets immobilized in the micro-columns;
e. migrating probes eluted from the micro-columns towards a detector constituted by a mass spectrometer;
f. analyzing each probe using a mass spectrometer.

As an alternative to the preceding method, it is possible to use the set of probes constituted by specific probes, the size of each specific probe for a target differing from the other probes and/or labeled by a specific fluorescence marker, detection being carried out after capillary electrophoresis of probes using a suitable spectrophotometer.

The invention also concerns a method for separating and assaying molecular targets contained in a complex mixture, said method comprising:
a. introducing a complex mixture containing molecular targets to be separated into a device of the invention comprising firstly, a network of capillaries allowing the complex mixture to be moved and secondly, two sets of electrodes in accordance with the description above;
b. applying an electric potential between the electrodes of the device, so that the targets can migrate from one end of the network of capillaries to the other end and so that the targets complementary to the probes can be hybridized;
c. in situ analysis or recovery followed by analysis of each target hybridized to a probe using a detector.

The implementation of this method is illustrated in the examples and Figures.

The invention also concerns a method for analyzing a transcriptome comprising using:
a. a set of magnetic particles on which the set of targets representative of a transcriptome to be analyzed is immobilized; and
b. a set of different types of probes in which each probe type of the set of probes is specific and complementary to one target type to form a stoichiometric mixture with said targets.

The invention concerns a method as herein defined, characterized in that each probe type of the set of probes is specific and complementary to a target type to form a stoichiometric mixture.

The invention also concerns a method as described above, characterized in that each probe type present in the mixture is identifiable in a non-equivocal manner by its molecular mass, which is obtained by combining three criteria: the empirical formula, the size and any labeling with heavy atoms.

The invention also concerns a method as described above, characterized in that each probe type present in the mixture is defined in a non-equivocal manner by its size and a fluorescence marker.

The method herein described, transcriptome analysis, may be transposed to the analysis of a proteome or to the analysis of the gain or loss of one or more genes in a patient. In these other analyses, the probes are also determined to be representative of the desired targets and each probe type of the set of probes is identifiable in a non-equivocal manner with respect to other probe types.

The following examples illustrate certain preferred embodiments of the devices of the invention and provide a better understanding of their uses without, however, limiting the scope of the invention.

The gold or ITO electrodes are etched onto a glass sheet.

The probes (spot or hybridization unit) are deposited on the electrodes or between the electrodes depending on the case. In the method, only the use of deposition onto the electrodes will be described.

Figure 8:
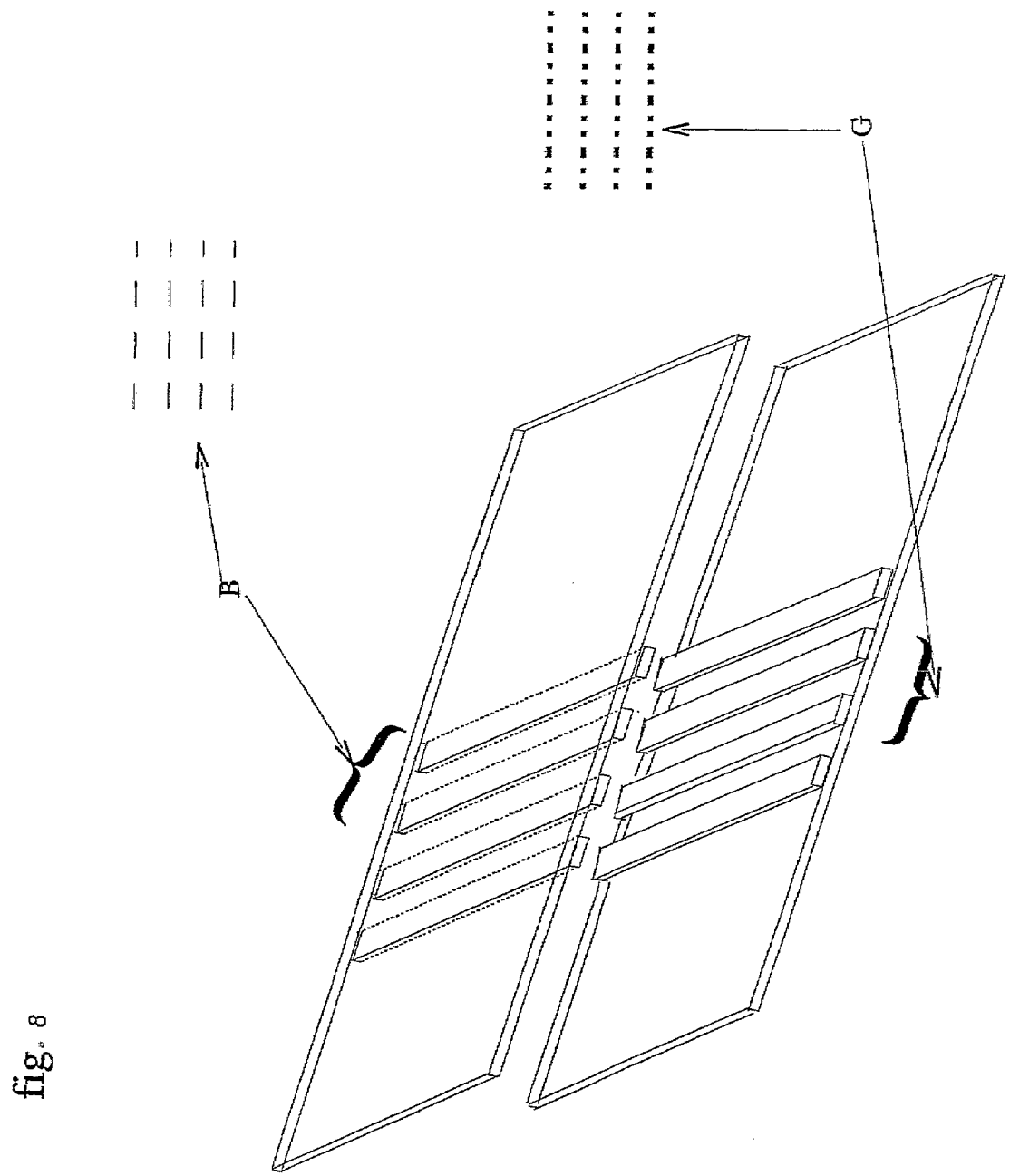

FIG. 8 illustrates an assembly of pairs of row electrodes

The row electrode pairs are obtained by disposing two sheets etched with electrodes face-to-face. One of the sheets is functionalized, the other is not.

Figure 9:
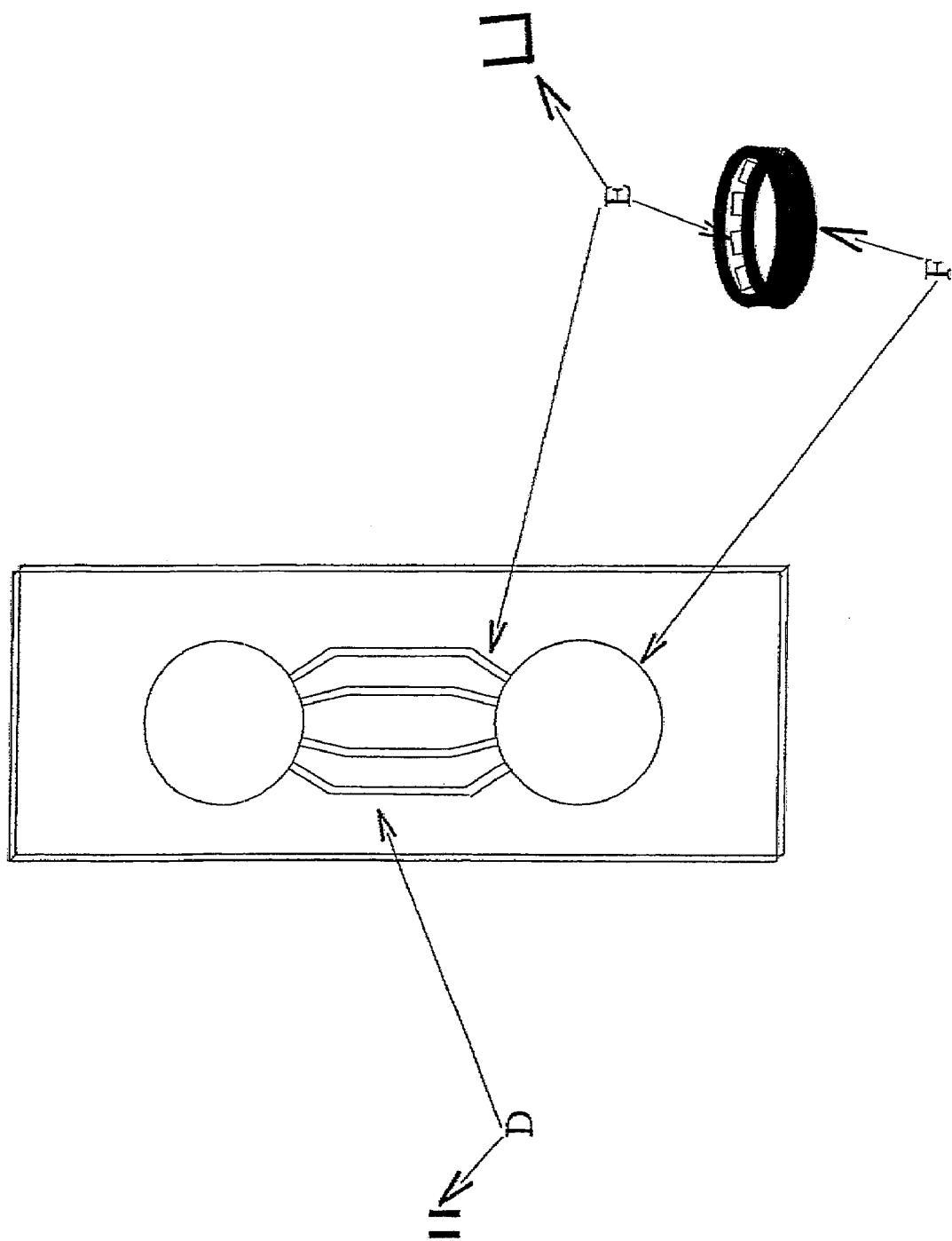

FIG. 9 illustrates a network of capillaries to be interposed between the two sets of functionalized and non-functionalized electrodes.

Figure 10:
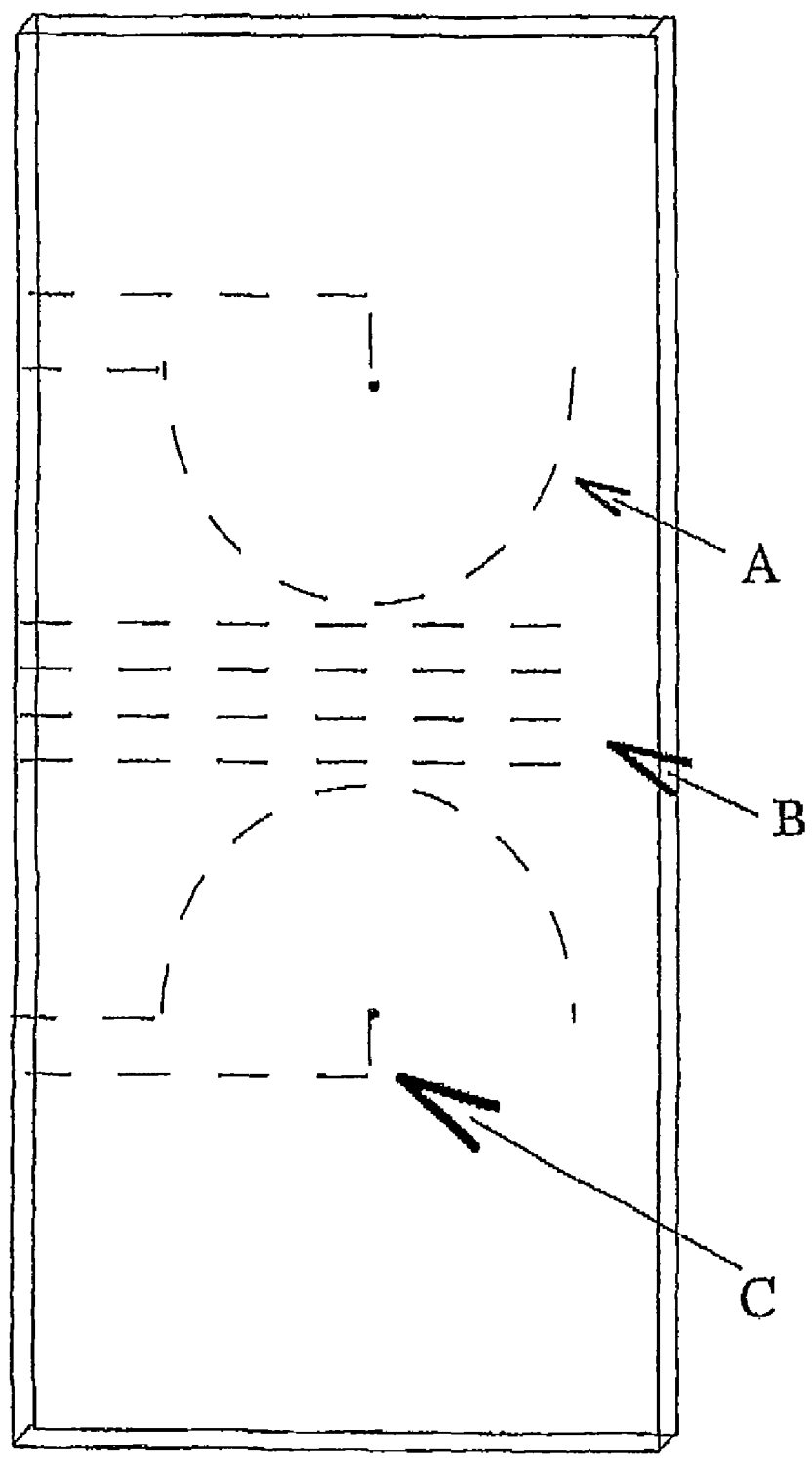

FIG. 10 illustrates a set of functionalized electrodes, completed by curved connection electrodes and the reservoir electrodes.

FIG. 11 illustrates an assembly of two sets of functionalized and non-functionalized electrodes around the capillary network.

Figure 12:
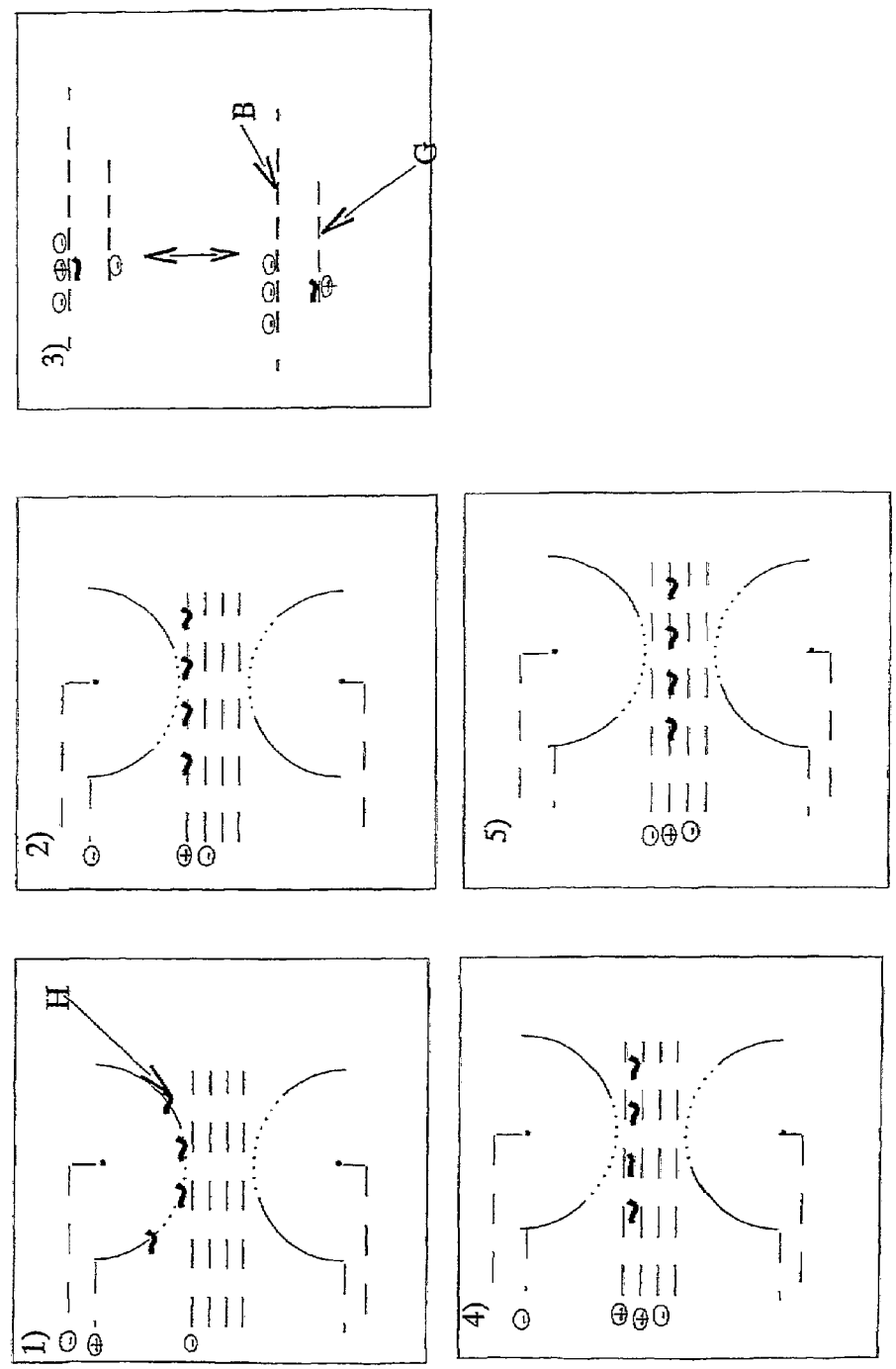

FIG. 12 illustrates a sequence of charges applied to the electrodes to cause the targets to migrate sequentially from one electrode to another, and thus from one spot to another.

Figure 13:
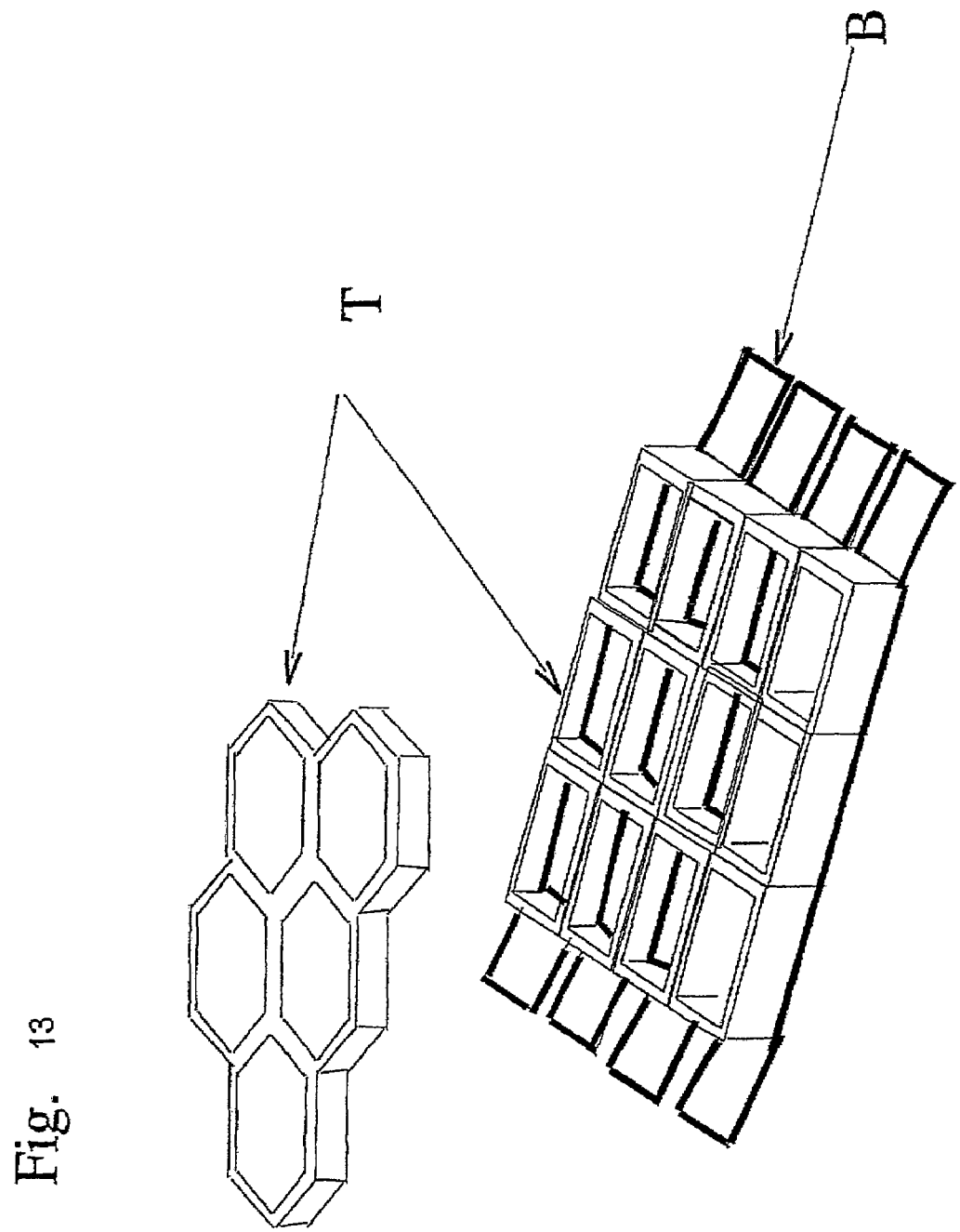

FIG. 13 illustrates semi-open cells with a floor constituted by the functionalized electrodes.

They open into the capillaries of the network of capillaries. These cells prevent dispersion of targets by diffusion.

Figure 14:
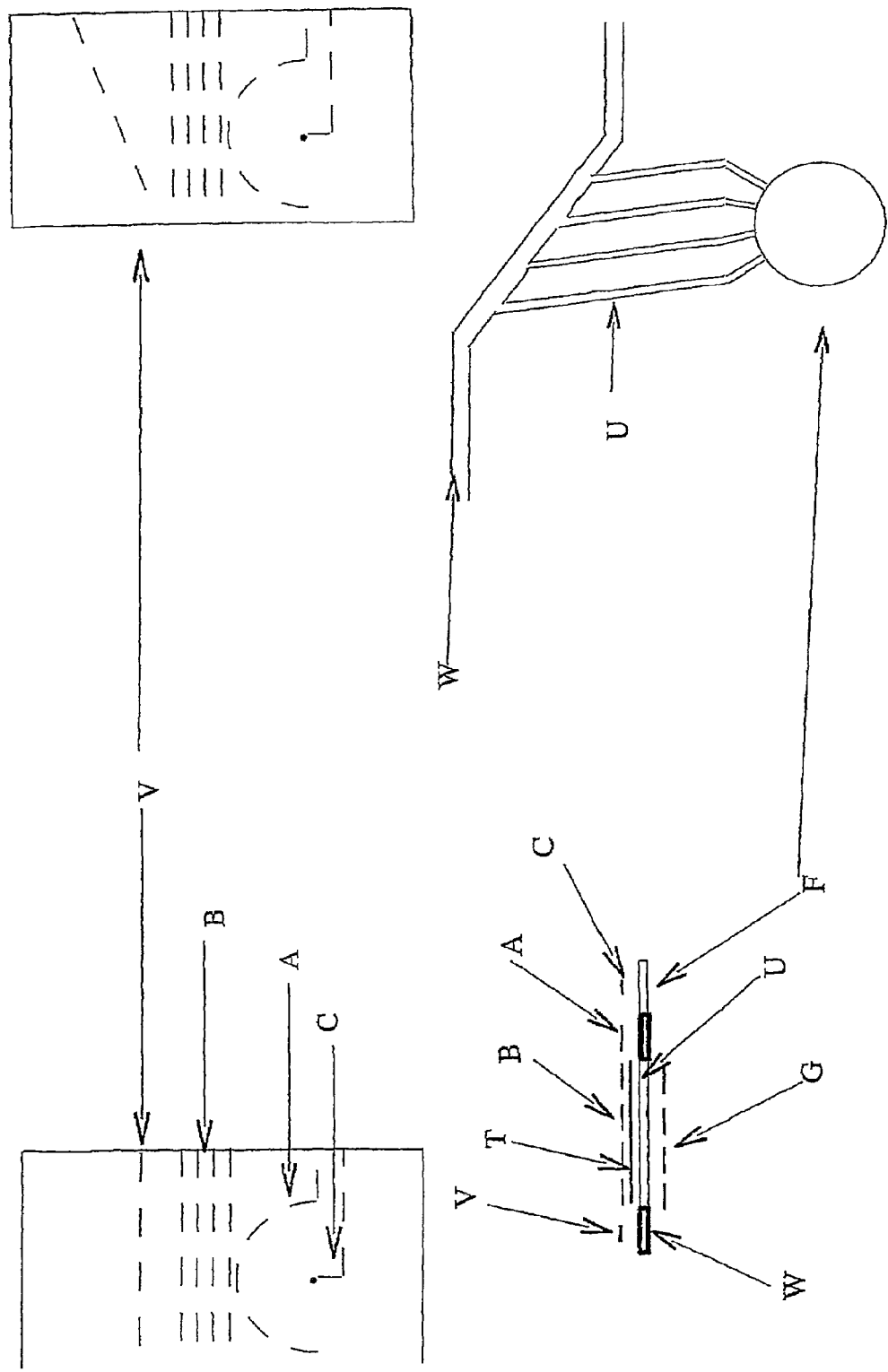

FIG. 14 illustrates a variation of the device with a single capillary network.

The second reservoir is removed to the benefit of a transverse channel and a delay system.

The second connection electrode (V) is rectilinear. It serves to define an impenetrable electrostatic barrier to the charged targets. When the electrode (V) projects with respect to the transverse channel (W), the delay effect is amplified. The second connection electrode allows the probes to be selectively displaced in the transverse channel.

Figure 15:
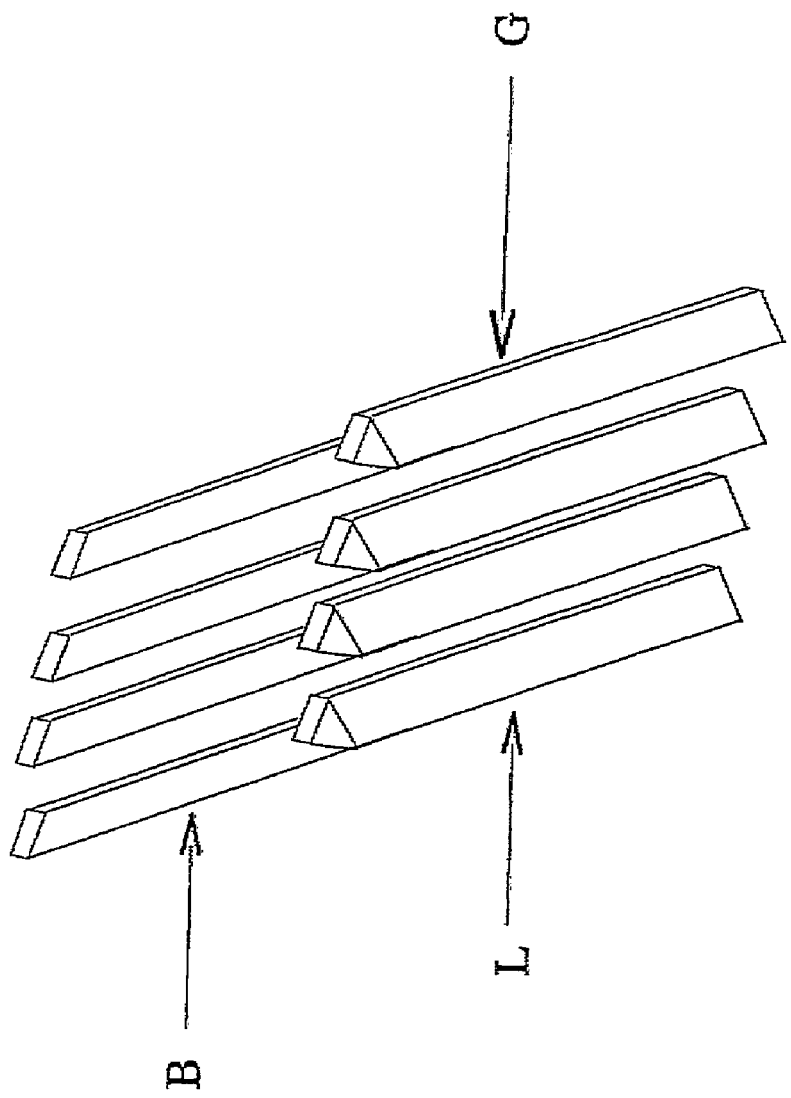

FIG. 15 illustrates a device for in situ SPR detection.

A trihedral prism is joined to the back of the non-functionalized electrode.

Figure 16:
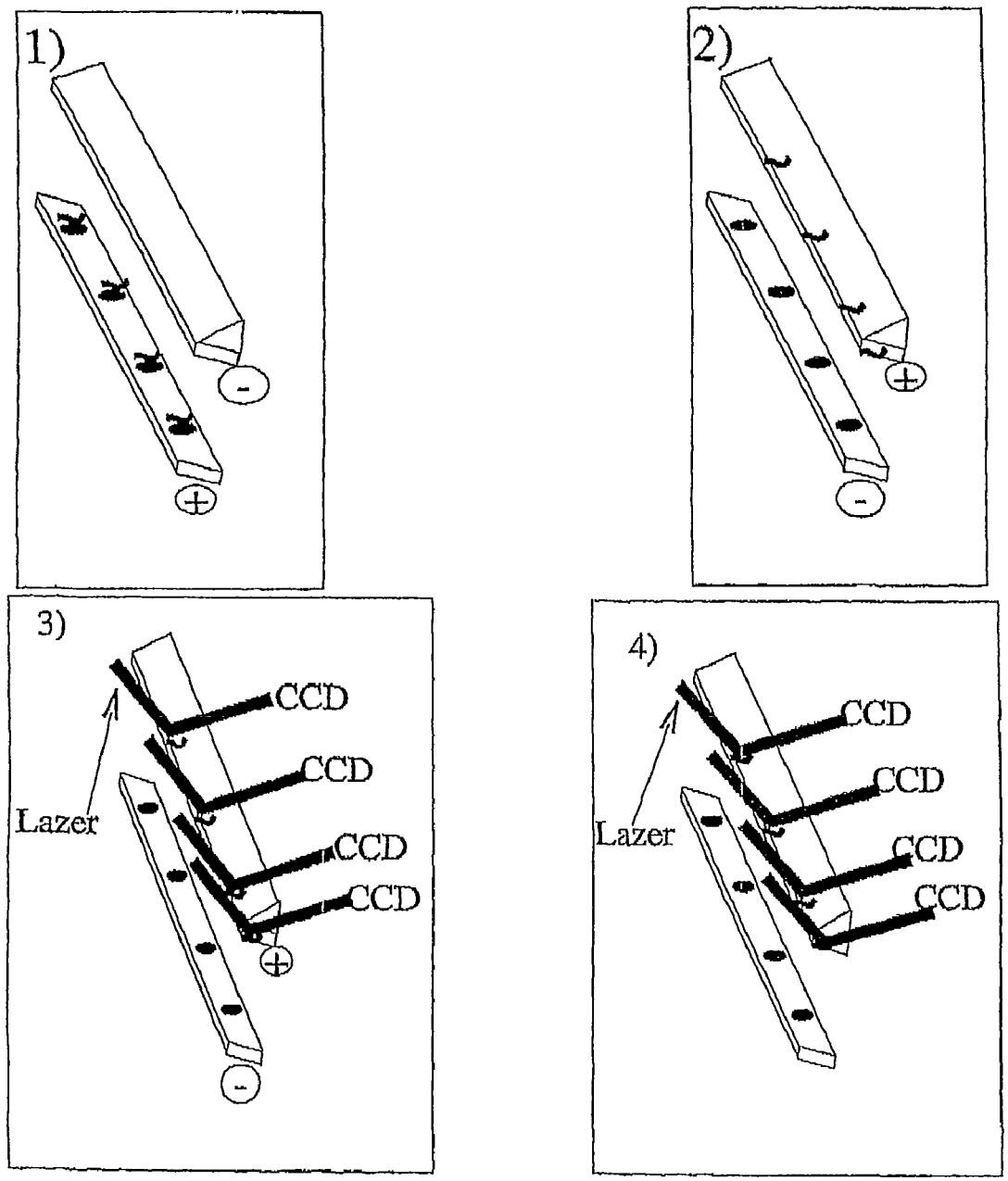

FIG. 16 illustrates a principle for SPR detection on the non-functionalized electrode.

1) the dehybridized targets are held in place by the electrode field;
2) the targets migrate by dint of the field to the non-functionalized electrode;
3) SPR detection takes place;
4) The current may alternatively be cut to improve detection.

FIG. 17 illustrates a device with two crossed sets of superimposed electrodes to carry out impedance measurements.

Figure 18:
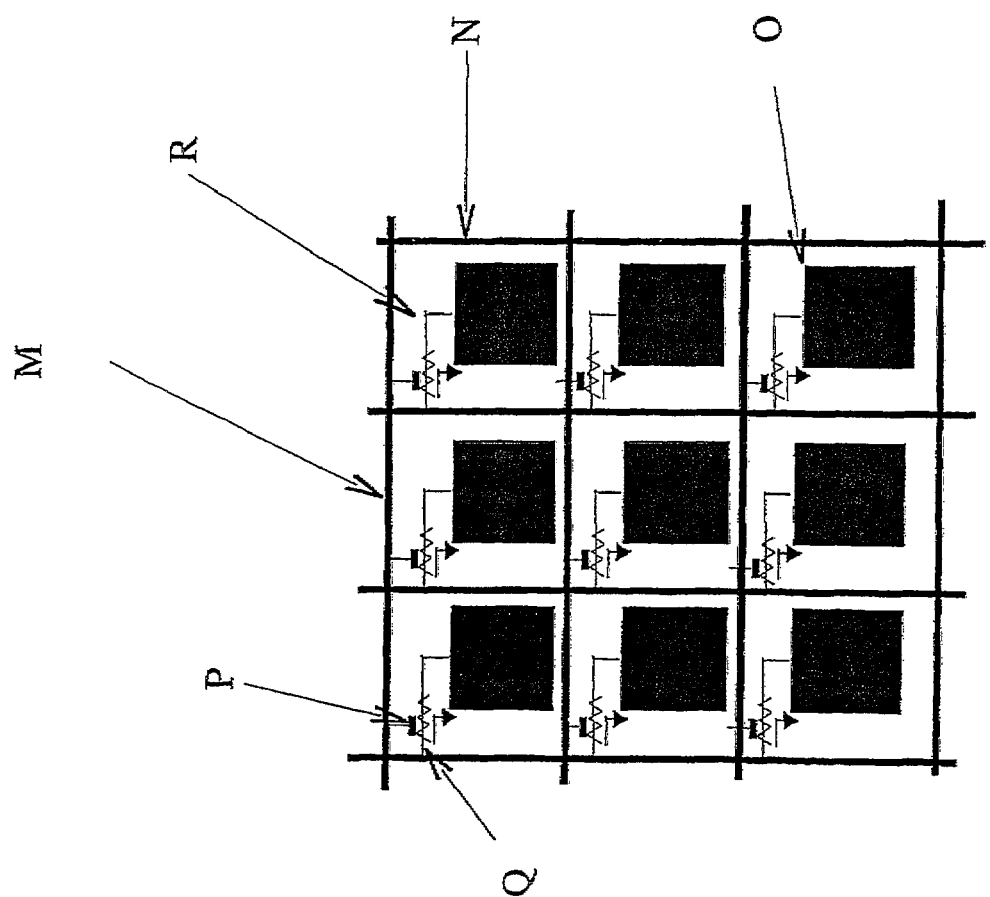

FIG. 18 illustrates a grid replacing the set of functionalized electrodes for discontinuous current impedance measurements.

Figure 19:
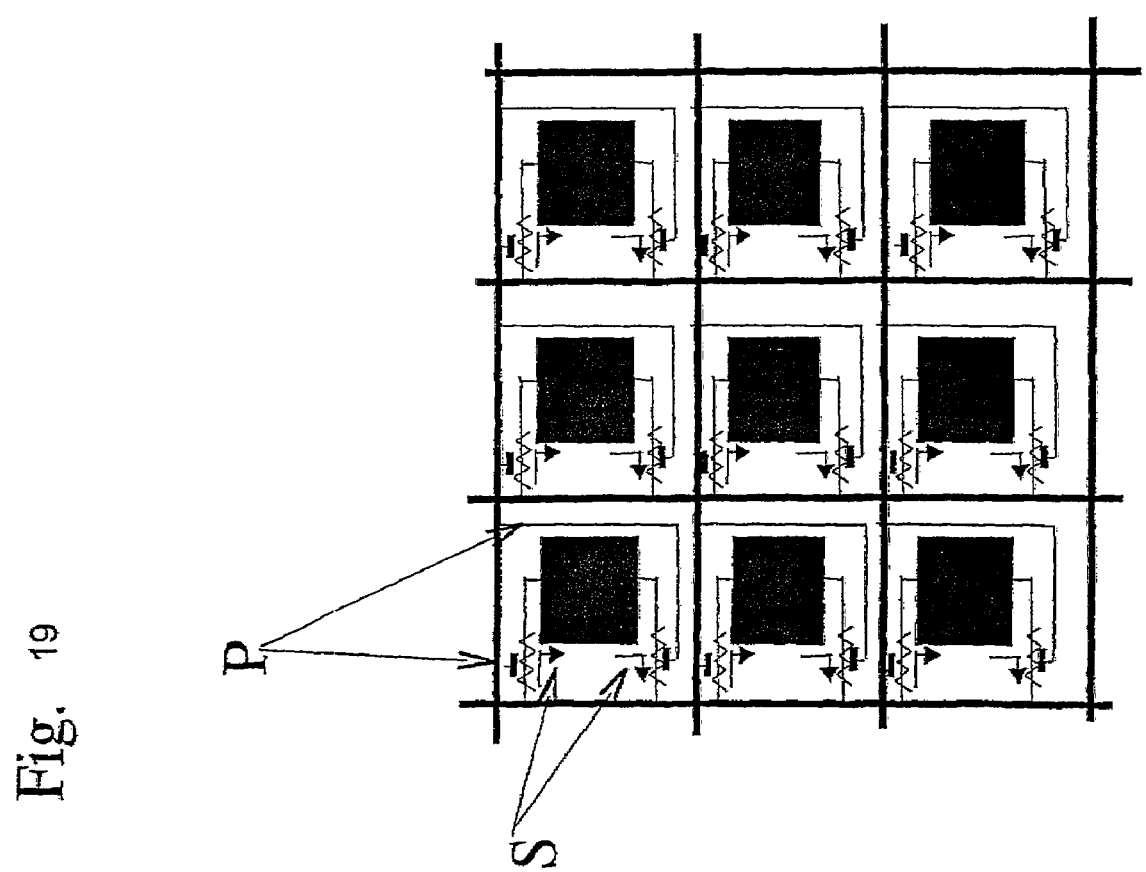

FIG. 19 illustrates a grid replacing the set of functionalized electrodes for alternating current impedance measurements.

EXAMPLES

Figure 1A:
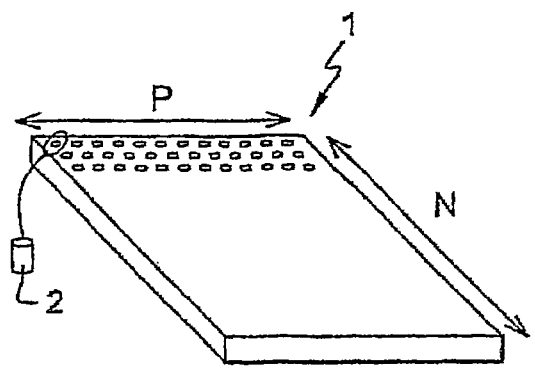
FIG. 1A is a top view of a matrix (1) of N rows and P columns of micro-columns molded into a suitable material.
Figure 1B:
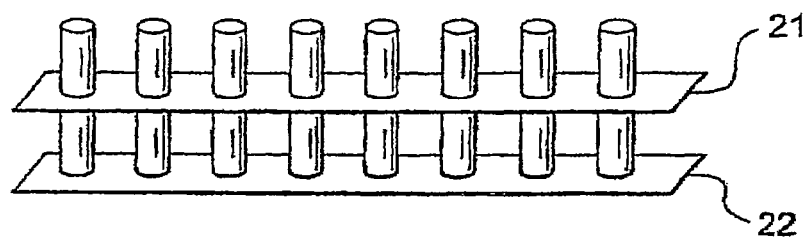
FIG. 1B represents a row of micro-columns connected via a median row electrode (21) and a distal row electrode (22).

1. Example of a Device for Detecting DNA or RNA Molecules Contained in a Biological Sample 1A The Micro-column Matrix The matrix of micro-columns (1) is constituted by N rows and P columns of 50 μm diameter, 100 μm long micro-columns, hollowed or molded into the thickness of a material of the glass, silicon or plastic type (FIG. 1A). The cells are perpendicular to the principal plane of the array. Each cell is filled with a polyacrylamide gel and the specific molecular probes are immobilized on particles the diameter of which is greater than the mesh size of the gel. The cells of each row of the micro-column matrix are connected via a common electrode forming a cell row electrode (21). This electrode is constituted by a thin layer of gold, median to the cells separating each of them into two half cells. A second set of electrodes, a mirror image of the median row electrodes. A second set of electrodes, a mirror image of the median row electrodes, is disposed at the outlet from the cells of the micro-column matrix, namely the distal row electrodes (22). Each distal row electrode is parallel to a median row electrode forming pairs of row electrodes (FIG. 1B). These pairs of electrodes allow the desired potential to be applied to each row of cells. The distal electrodes are produced in the same manner as the median electrodes.

1B The Staged Capillary Network

Each cell is connected via two channels to two staged networks of capillaries located respectively above and below the plane of the cells (see FIG. 2): the upper network of capillaries is constituted by N parallel capillaries (upper capillaries) (3); the lower network is constituted by P parallel capillaries (lower capillaries) (4); the N/P disposition may clearly be reversed between the two capillary stages. One capillary of the upper network is connected to P cells of a row of the micro-column matrix, or respectively the same capillary of the lower network is connected to N cells of a column of the micro-column matrix. The connections are produced by the connection channels described above, so that the orientation between the two networks of lower and upper capillaries is perpendicular. For this reason, each capillary of the upper network is connected with all of the capillaries of the lower network by a row of P cells of the micro-column matrix. In contrast, each capillary of the lower network is connected to all of the capillaries of the upper network by a column of N cells of the micro-column matrix.

The capillaries have a diameter in the range 1 to 100 μm. All of the capillaries of the upper network open into a transverse capillary (31) (upper transverse channel) with a diameter in the range 2 to 1000 µm. The upper transverse channel thus connects all of the capillaries of the upper network; it is perpendicular to the direction of the upper network. The ends of the capillaries of the upper network opposite to the transverse channel stop at the last connection with the $P^{th}$ and last cells of the cell rows of the micro-column matrix. All of the capillaries of the lower network open into a transverse capillary (41) (lower transverse channel) with a diameter in the range 2 to 1000 µm. The lower transverse channel thus connects all of the capillaries of the lower network. The capillaries of the lower network are produced so that the trajectory between the connection with the first cell of a cell column and the lower transverse channel has a different length from one lower capillary to another. This portion of a capillary of the lower network is termed the delay. The delay is obtained using a lower transverse channel making an angle other than 90° with the lower capillary network. Depending on the angle selected, the delays increase or decrease between successive lower capillaries.

Figure 2:
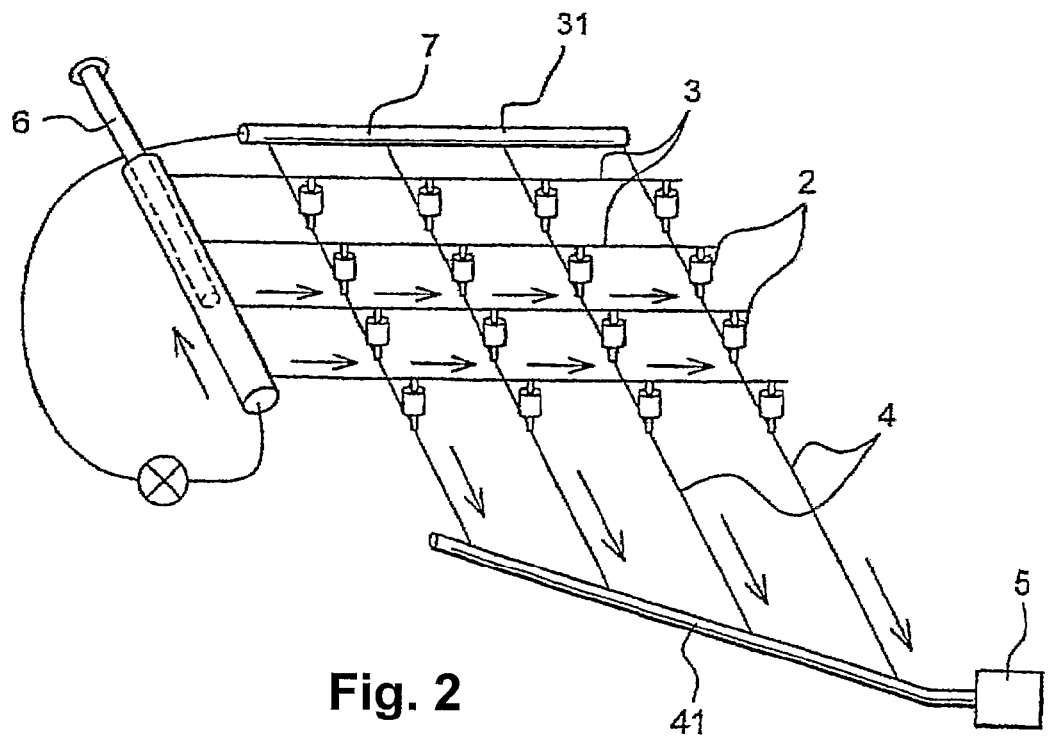
FIG. 2 shows a diagrammatic view of a device comprising a matrix of micro-columns (2), an upper capillary network (3) connected to the upper transverse channel (31) provided with a piston (6), a lower network of capillaries (4) connected to a lower transverse channel (41) and to a detector (5). The device also comprises a secondary transverse channel (7) to facilitate movement of the streams during the hybridization and/or rinsing steps.

The end of the capillaries of the lower network of capillaries opposite to the transverse channel is connected to a second transverse channel (7) (secondary lower transverse channel) to allow a flow to be established between the two, lower and upper, capillary networks through the cell matrix. The principal lower transverse channel is filled with a liquid capillary electrophoresis gel to produce capillary electrophoresis therein; it is thus possible to establish a closed cycle flow between the upper transverse channel and the secondary lower transverse channel (FIG. 2).

Electrodes are disposed at the upper and lower transverse channels.

The upper transverse channel is provided with a piston (6) which may or may not be threaded, which allows the number of rows of cells through which the stream will pass to be selected. As it is drawn back, the piston mobilizes more and more rows of cells of the micro-column matrix.

1C Detector

Detection of molecules at the outlet from the lower transverse channel is carried out using a mass spectrometer (5).

Figure 3:
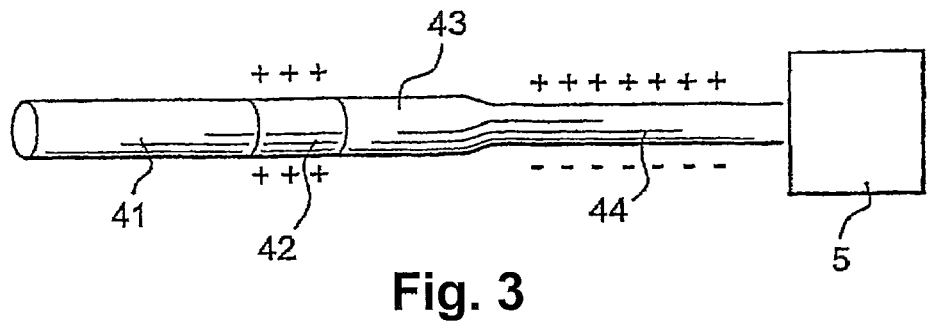
FIG. 3 is a detailed view of the connection of the lower transverse channel (41) comprising the lower channel electrode (42), a piezoelectric pipette (43), the ElectroSpray (44) and the detector.

The lower transverse channel is contiguous with the ElectroSpray ionization detector (ESI) (44) of a mass spectrometer (FIG. 3). It is connected to the detector via a piezoelectric or thermal pipette (43) which allows regular injection into the Electro Spray.

2. Example 2

Pistonless Device

The example below illustrates a further embodiment of the device of the invention adapted to separate and analyze nucleic acid molecules contained in a biological sample and allowing denaturing of molecular targets retained in the micro-columns and their migration to the detector solely by using electric fields.

The micro-column matrix and the network of capillaries are substantially identical to Example 1 with the following exceptions:

The device does not comprise a piston at the upper transverse channel. Instead, the lower transverse channel and the upper transverse channel are connected to denaturing buffer reservoirs containing an ammonium hydroxide salt ($NH_4OH$).

3. Example 3

Preparation of a Micro-Column Containing a Set of Nucleic Acids Representative of a Transcriptome and its Use in Analysis of a Transcriptome Each micro-column of the device of the invention, such as that described in Example 1 or 2, comprises a support or particles on which the set of nucleic acids representative of a transcriptome to be analyzed (DNA, RNA or oligonucleotide, etc) are immobilized.

To avoid the presence of a long polyA tail, reverse transcription of the messenger RNA sample to be analyzed is carried out from primers such as $5'(T)_{19}X3'$ where X may be A, C or G. Reverse transcription is thus carried out from the first nucleotide which is not A encountered after the polyA tail.

To obtain a cDNA sample representative of a genome fixed on a support or a particle, the primers described above are initially fixed onto said support or said particles before reverse transcription. The reverse transcription products may also be grafted onto the support after reverse transcription. Grafting may be ensured by biotin-avidin pairings using $5'(T)_{19}X3'$ primers biotinylated at the 5' end (it is also possible to use chemical complexing between the particles and the targets).

The invention concerns a device for separating and/or detecting a plurality of molecular targets in solution in a complex mixture, said device comprising a set of magnetic particles onto which all of the targets representative of a transcriptome to be analyzed are immobilized, and a set of probes.

Each probe type of the set of probes is specific and complementary to a target type to form a stoichiometric mixture.

These particles or support containing all of the cDNA representative of a genome are then disposed M a micro-column of the device of the present invention. A micro-column array is thus obtained, each micro-column of which can analyze a transcriptome, using the following method:

The device is used with a set of probes in which each probe type composing the mixture is specific and complementary to one target type and one alone from the target types immobilized in the micro-columns, to form a stoichiometric mixture.

Each probe type present in the mixture is then identifiable in a non-equivocal manner by its molecular mass. This molecular mass specificity is obtained by combining three criteria: the empirical formula, size and any labeling with heavy atoms. The combination of these three criteria allows an astronomical number of probes to be produced. For a DNA polymer size M such that M=n+m+l+j, it is possible to produce the following number for the empirical formula ($A_n C_m T_l G_j$) the (n+m+l+j)!/(n!*m!*l!*j!).

The complementary probes specifically hybridize to target molecules retained on the support or particles; this is the separation step. Once the system has been rinsed and the non-hybridized probes have been eliminated, the probe molecules hybridized at the support or the particles are denatured in a controlled manner. It is then possible to quantify each type of hybridized probe molecule on the support or on the particles containing the immobilized targets.

To minimize non-specific hybridizations, the sequences are hybridized in the presence of small nucleotide polymers $(X)n$ in which X represents A, T, G or C and n varies from 3 to 7 nucleotides to form all possible sequences of n nucleotides.

This method may also be applied to proteins in the context of studying a proteome. The mixture of proteins to be studied is fixed to a support or to particles. The targets are constituted by antibodies or any other specific ligand; the molecular mass of each probe types will allow their identification in a non-equivocal manner.

To avoid a lack of discrimination between different types of probes having identical molecular masses, the probes may be coupled with inert molecules which modify the molecular mass of the probe. To further increase discrimination and detection, capillary chromatography is carried out before injection into the mass spectrometer. This capillary chromatography allows the probes to be separated according to size. The mass spectrometer and capillary electrophoresis are coupled with a piezoelectric pipette.

An alternative to the above embodiment consists of distinguishing the probes using fluorescence markers. Each probe type is defined in a non-equivocal manner by its size and a fluorescence marker. The combination of these two criteria can produce a degree of complexity of the order of a thousand by combining five different fluorescence markers, for example, with probes the sizes of which are staggered between 20 and 200 bases. It is clearly possible to increase the complexity of the mixture of probes by increasing the range of sizes for the probes and the number of fluorescence markers used.

The method is intended to be use directly in solution using a set of magnetic particles on which all of the targets are immobilized, representative of a transcriptome to be analyzed, and a stoichiometric set of probes as described above. The magnetic particles act to isolate the hybridized probes. In fact, the hybridized particles are isolated by a magnetic field produced by a simple magnet. Once the system has been rinsed and the non-hybridized probes eliminated, the hybridized probes are dehybridized in a controlled manner, and analysis of the eluate by one of the methods described above can define the composition of the analyzed transcriptome.

This method can substitute for a conventional DNA array, in particular in studies of the transcriptome and CGH (comparative genomic hybridization).

4. Example 4

Use of a Micro-Column Array as Described in Example 1 to Analyze RNA Samples

The device described in Example 1 can analyze a mixture of nucleic acid molecules. The analysis may be carried out from a simple cellular RNA extract but also from two different extracts.

To analyze two different RNA extracts with detection by mass spectrometry, at least one of the two mRNA populations is labeled. Labeling is carried out by reverse transcription with incorporation of a heavy isotope. The heavy isotopes are selected from $O^{18}$, $O^{17}$, $N''$, $C^{13}$, $H^2$ or any other heavy isotope which may be differentiated from the mass of the common form. Said heavy isotopes are incorporated into the nucleotides used in synthesizing nucleic acids. The second population of mRNA to be analyzed is reverse transcribed to cDNA without incorporating heavy atoms or incorporating different heavy atoms which differs from those of the first population.

To avoid confusion with any decomposition products, 5'$(T)_{19}$X3' primers in which X may take the values A, G or C are labeled with heavy atoms which differ from those which may be used for the residue of the molecule in the case of detection by mass spectrometry. On detecting by fluorescence, those primers are labeled by chromophores.

Reverse transcription is stopped abruptly at an early stage and since the elongation time is identical for all of the cDNA obtained, cDNA molecules are obtained with a restricted size which are more easily identifiable by mass. This method may also be used to prepare cDNA targets for use with conventional DNA arrays.

Once the two cDNA populations have been obtained, they are mixed in an equimolar manner (it is also possible to treat heterogeneous mRNA/cDNA mixtures). The mixture is introduced into a closed circuit which circulates several times in each micro-column (see FIG. 2). During passage in the micro-columns, the targets hybridize to complementary probes. Circulation inside the closed circuit homogenizes the mixture after each passage in the micro-columns. A resistor located at an admission tube, for example, can regulate the temperature of the hybridization solution, but also can produce thermal variations during a hybridization cycle to control the hybridization specificity. A sonication chamber can optionally homogenize the size of the molecules to be hybridized by breaking the target cDNA into smaller molecules, since probes constituted by oligonucleotides (20 to 100 bp) facilitate the hybridization effect for targets with an equivalent size.

Once hybridization has been carried out, the circuit is opened and rinsed well (rinsing steps) with a solution eliminating non-hybridized or not specifically hybridized molecules.

Figure 4:
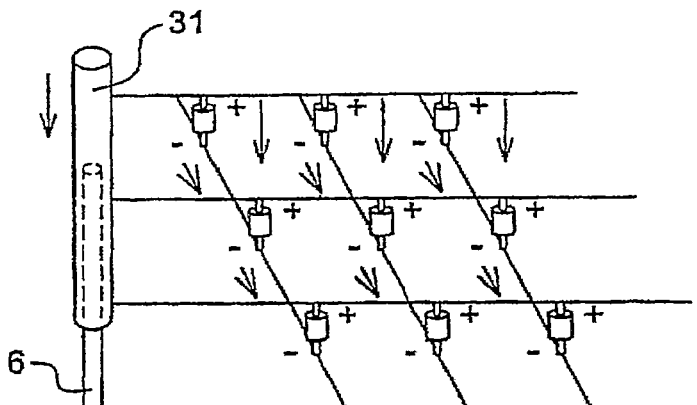
FIG. 4 represents the polarities of the electrodes during the step for denaturing negatively charged molecular targets using a device provided with a piston. The metal piston (6) is covered with negatively charged electrodes. The denaturing solution is introduced to the free end of the upper transverse channel (31), the arrows indicating the direction of motion of the flow. The electrodes are positive at the micro-columns (+) and negative at the micro-column outlet (−).

The system is then coupled to the ElectroSpray of a mass spectrometer, and an electric potential difference is established between the pairs of row electrodes of the matrix micro-column, which are positive at the median level and negative at the distal level. Similarly, an electric potential difference is established at the electrodes of the transverse channels, negative at the upper transverse channel and positive at the lower transverse channel. Because of the polarity of the electrodes, the hybridized molecules are maintained in each hybridization cell. The piston is disposed so that circulation can only occur between the two, upper and lower, networks via the micro-columns of the first row of matrix micro-column (FIG. 4). A denaturing solution the temperature of which is controlled by the resistance (located in the upper transverse channel, for example) is then injected as a laminar flow and diffuses through the micro-columns of the first row, the closest to the lower transcription channel, the piston preventing access to the other rows of micro-columns. The denaturing agent denatures the probe-target complexes; the electric field prevents diffusion of targets outside the cells.

Thermal denaturing is also envisageable as an alternative. By increasing the temperature of the buffer in each micro-column, denaturing of the duplex formed between the fixed probe and the target occurs and the target passes into solution while the probe remains fixed on the matrix.

Figure 5:
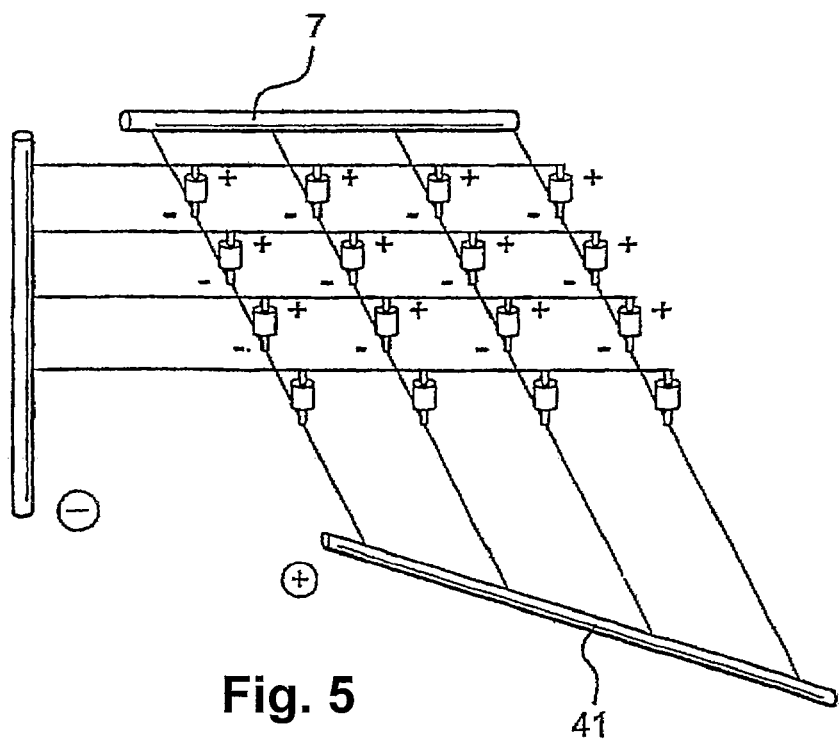
FIG. 5 shows the polarities of the electrodes during the step for migration of molecular targets from the first row. The difference in electric potential at the electrodes of the first row is removed. The lower transverse channel (41) is filled with gel. The device also comprises a secondary transverse channel (7).

The electric field between the electrode pair of the first row is then reversed or simply cut off; the potential difference between the electrode pair of the transverse channels is maintained (FIG. 5). The targets of each micro-column of the first row then pass into the corresponding capillaries of the lower network; the probes are transported or migrate by electrophoresis through these capillaries to the lower transverse channel. The targets from the various micro-columns arrive in the lower transverse channel at different times as a function of the respective delays of the capillaries of the lower network. In fact, the various targets arrive in the capillaries of the detector (ElectroSpray) coupled to the lower transverse channel at different times for analysis. So that there is no mixing between the targets from the various micro-columns, it is in general necessary to operate using a very slow laminar flow.

The use of several probes per micro-column allows all of the splicing forms of the gene to be determined.

5. Example 5

Use of a Micro-Column Array as Described in Example 2 to Analyze RNA Samples

In the following method, the fluids are not circulated in the capillaries to denature the targets and migrate them towards the mass spectrometer.

Figure 6:
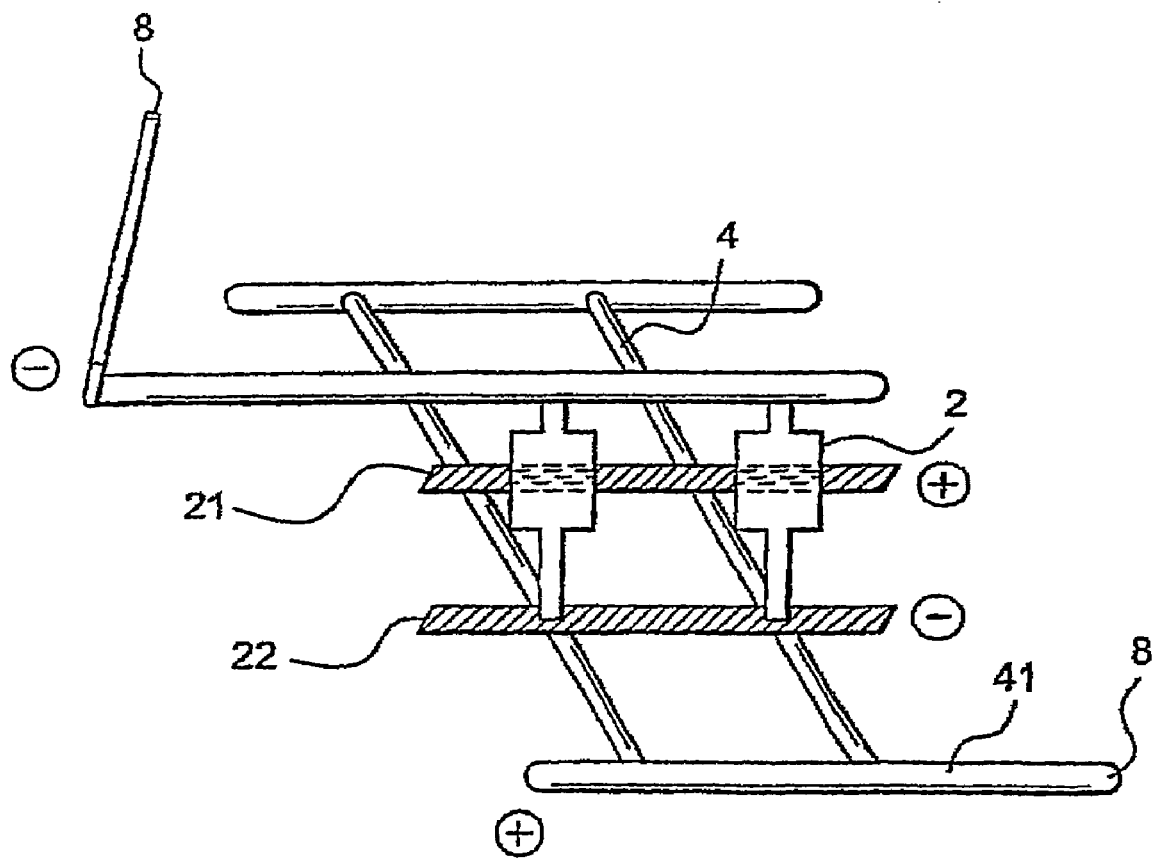
FIG. 6 illustrates the step for denaturing molecular targets charged into the device using reservoirs (8) of denaturing buffers containing a chaotropic agent capable of migrating in an electric field.
Figure 7:
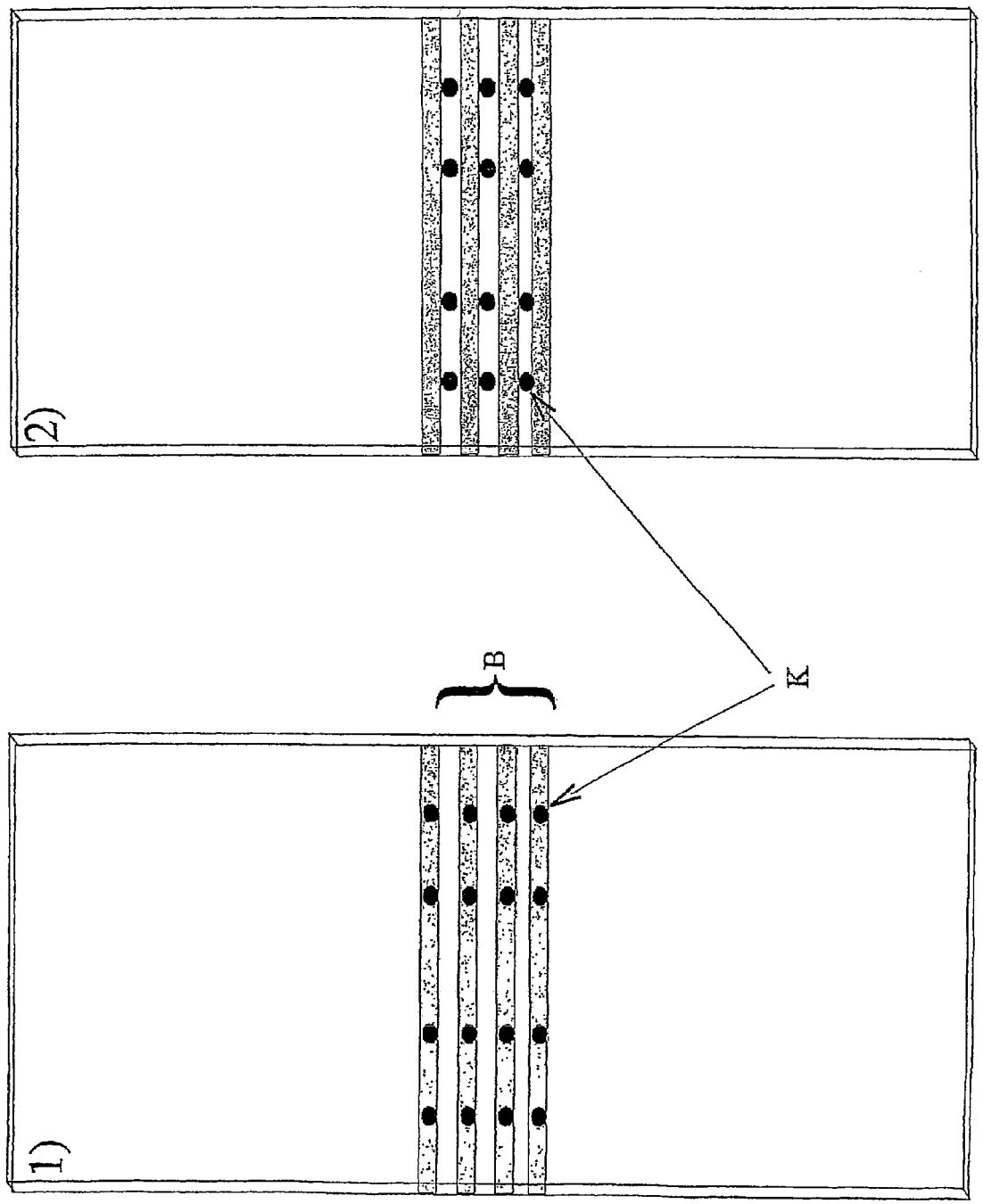
FIG. 7 illustrates an example of a set of functionalized electrodes grafted with probes.

In this method, the device described in Example 2 is used. The operation of the hybridization and rinsing steps is identical to that described in Example 4. After hybridization and rinsing, the upper transverse channel is connected to the buffer reservoir containing the chaotropic agent which is capable of migrating in a buffer electric field; the lower transverse channel is connected to a second reservoir containing the same buffer. The electrodes of the upper and lower transverse channel and the distal row electrodes are maintained at a negative potential with respect to the median row electrodes which are maintained at a positive potential. Migration of ions and chaotropic agents, to the anode and to the cathode, the pH of the buffer and the potential difference causes denaturing of the probe-target biopolymer complexes (FIG. 6).

The probes remain fixed on the matrix because of the strong bond with it; the negatively charged free targets also remain at the level of the positively charged median row electrodes. Once the probe/target complexes have been denatured, the electrodes of the transverse channels are taken to an electric differential which is negative for that of the upper transverse channel and positive for that of the lower channel, the electric potential being kept positive for median and negative electrodes for the distal electrodes; the targets are thus confined in an electrostatic chamber in each micro-column, prohibiting any migration.

The potential differences between the row electrodes of the micro-column matrix are then removed row by row, causing successive migration of the targets of each row into the capillaries of the corresponding lower network by electrophoresis. The targets migrate to the lower transverse channel as a function of the respective trajectory distances of their capillary. Analysis is carried out at the outlet from the lower transverse channel.

6. Example 6

Micro Sequencing Biopolymer Separated and Isolated in Each Micro-Column

The methods of the invention allow nucleic acids or protein targets separated and analyzed in the mass spectrometer to be sequenced.

Micro-sequencing consists of carrying out random cleavage in the nucleic acid sequence then identifying the resulting products by mass spectrometry. The random cleavages may be chemical, physical, mechanical or enzymatic. As an example, enzymatic cleavage may be carried out by the action of an enzymatic mixture constituted by enzymes fixed in a micro-column, said micro-column being disposed, for example, between the detection capillary and the lower transverse channel. When the biopolymers traverse this micro-column, they are partially degraded. Analysis of the degradation products allows the sequence to be deduced. The enzymes, such as endonucleases for nucleic acids or endopeptidases for proteins can, for example, produce random cleavages in these biopolymers. The use of exonucleases for nucleic acids and exopeptidases for proteins allow partial digestion. Analysis of the products of said reactions can produce the sequence of biopolymers specifically retained in each of the micro-columns. The chemical cleavages are obtained by controlled chemical degradation of the biopolymers using an acid, a base or any other chemical product.

Mechanical degradation is carried out, for example, using ultrasound, microwaves or micro-frequencies which are capable of segmenting biopolymers. Finally, physical decomposition may be carried out by a stream of electrons or by bombardment with heavy atoms which will interact with the biopolymer. These treatments allow the biopolymer to be fractured into combinations which can be predicted, such as the rupture of phosphate bonds for nucleic acids and peptide bonds for proteins. The treatments will be carried out to statistically induce only one random cleavage per molecule. To determine the sequence of the biopolymers, it is necessary to have a marker available at least one of their ends. The study of all of the decomposition ions obtained comprising this marker allows the sequence to be established. Either the end marker exists naturally in the biopolymer, or it is introduced artificially. As an example, the 3' ends of the mRNA s systematically comprise a polyA tail. This polyA tail may act as end markers: cDNA is obtained by reverse transcription with primers such as $5'(T)_{19}X3'$ in which X may be A, C or G. Reverse transcription is thus carried out from the first nucleotide which is other than A encountered after the polyA tail. To avoid any confusion with any decomposition products, the $5'(T)_{19}X3'$ primers are labeled with heavy atoms, which differ from those which may be used for the remainder of the molecule. Knowing the exact mass of the marker, it will be easy to deduce the succession of residues in the sequence from the cleavage products. In the case of proteins, labeling the N terminal end with compounds such as phenyl isothiocyanate, 1-fluoro-2,4-dinitrobenzene or densyl chloride allows the sequence to be determined. It is also possible to carry out double labeling of the biopolymer at each of its ends to increase the resolving power of the method. In complex cases, MSMS methods enable the molecular ions to be analyzed to be selected in a second step such as in the case of multimeric proteins. Finally, it is possible to determine the sequence of biopolymers directly by analyzing the successive decomposition products, as allowed by MSMS methods, the end markers of the sequences being determined using N terminal and C terminal ends for proteins, for example.

7. Use of a Micro-Column Array to Analyze Mixtures of Polypeptides

The devices are produced in a manner similar to those described in Example 1 or 2. Each micro-column of the matrix is filled with antibodies specific to one type of polypeptide. The antibodies are specific to the native or denatured proteins. The antibodies are fixed directly to the wall of the cells or to particles retained in each cell. As for nucleic acids, it will be possible to use antibodies bound to a pyrrole molecule. All of the methods applied for probes bound to pyrrole which have been described for nucleic acids are applicable to antibodies bound to pyrrole. The cellular extracts of polypeptides are complexed by producing a closed circuit with the micro-columns networks. This allows the formation of specific antigen/antibody complexes in each micro-column. To elute the polypeptides retained in each micro-column, it is necessary to use buffers allowing proteins to migration, only as a function of their size. These buffers also destroy the antibody/antigen complex. To this end, buffers based on SDS (sodium dodecyl sulfate) can be cited, which allow all of the proteins to migrate towards the positive poles, regardless of their isoelectric point.

DESCRIPTION OF FIGURES

The references in the Figures are defined as follows:
A=curved connection electrode (for example a glass sheet with transparent ITO electrodes)
B=functionalized row electrodes (for example a glass sheet with transparent ITO electrodes)
C=reservoir electrode (for example a glass sheet with transparent ITO electrodes)
D=capillary without floor or top (for example hollowed into Kapton): median plane
E=capillary without floor but with top (for example hollowed into Kapton): median plane
F=reservoir without floor or top (for example hollowed into Kapton): median plane
G=non-functionalized row electrodes (for example a glass sheet with transparent ITO electrodes)
H=non-hybridized targets
I=functionalized electrodes
J=non-functionalized electrodes
K=spots of probes: hybridization unit
L=prism
M=Horizontal gate electrode
N=vertical source electrode
O=spot electrode
P=gate
Q=source
R=drain
T=cell without base or top
S=direction of movement of current
U=network of capillaries with delay
V=connection row electrode for analysis
W=secondary transverse channel.

The invention claimed is:

1. A device for separating and/or detecting a plurality of molecular targets in solution in a complex mixture, said device comprising:
   a. a set of magnetic particles on which a set of molecular targets having different types and representative of a transcriptome or a proteome to be analyzed is immobilized; and
   b. a set of probes, wherein each probe comprises a nucleic acid sequence and is specific one type of molecular target of the set of molecular targets to form a stoichiometric mixture,
   wherein the set of probes is in solution in a mixture, and each probe has a molecular mass which is predetermined and which is different from the molecular masses of the other probes so that each type of probe is identifiable in a non-equivocal manner by its molecular mass, the molecular masses of the probes being predetermined and differentiated by combining three criteria of empirical formula, size and labeling with heavy atoms of the nucleic acid sequences of the probes.

2. The device according to claim 1, wherein the set of magnetic particles is inside one micro-column of a micro-column matrix.

3. The device according to claim 2, wherein the micro-column matrix comprises at least one row of micro-columns,
   a first row electrode that is median to the micro-columns and that separates each of the micro-columns in two half micro-columns, and
   a second row electrode that is parallel to the first row electrode and that is disposed at an outlet of the micro-columns.

4. The device according to claim 3, wherein each micro-column is connected via two channels to two staged networks of capillaries, which are located respectively above and below a plane of the micro-columns.

5. The device according to claim 4, wherein capillaries of the network of capillaries located below the plane of the micro-columns open out at a first end into a first lower transverse channel and at a second end into a second lower transverse channel.

6. The device according to claim 5, wherein the first lower transverse channel makes an angle other than 90° with the network of capillaries located below the plane of the micro-columns.

7. The device according to claim 4, wherein capillaries of the network of capillaries located above the plane of the micro-columns open out into an upper transverse channel.

8. The device according to claim 7, wherein the upper transverse channel is provided with a piston.

9. The device according to claim 1, wherein the set of molecular targets is a set of RNA and/or DNA molecular targets in a biological sample.

10. A method of detecting and/or assaying specific RNA and/or DNA molecular targets contained in a biological sample, which comprises contacting said biological sample with a device according to claim 1, wherein the probes are molecular probes selected so that they specifically hybridize with a type of said RNA or DNA Molecular targets contained in the biological sample.

11. The method according to claim 10 for the comparative analysis of specific RNA and/or DNA molecular targets contained in two biological samples.

12. A method for analyzing a transcriptome, comprising the use of:
   a. a set of magnetic particles on which a set of targets having different types and representative of a transcriptome to be analyzed are immobilized; and
   b. a set of probes having different types, wherein each type of probe is specific and complementary to one type of molecular target of the set of molecular targets to form a stoichiometric mixture, and
   wherein the set of probes is in solution in a mixture, and each type of probe is identifiable in a non-equivocal manner by its molecular mass, which is obtained by combining three criteria of empirical formula, size and labeling with heavy atoms.

* * * * *